United States Patent
Cook et al.

(10) Patent No.: US 6,740,645 B1
(45) Date of Patent: May 25, 2004

(54) 17β-ACYL-17α-PROPYNYL-11β-(CYCLIC AMINO) ARYL STEROIDS AND THEIR DERIVATIVES HAVING ANTAGONIST HORMONAL PROPERTIES

(75) Inventors: C. Edgar Cook, Staunton, VA (US); John A. Kepler, Raleigh, NC (US); Jill M. O'Reilly, Durham, NC (US)

(73) Assignee: Research Triangle Institute, Research Triangle Park, NC (US)

( * ) Notice: Subject to any disclaimer, the term of this patent is extended or adjusted under 35 U.S.C. 154(b) by 0 days.

(21) Appl. No.: 09/389,212

(22) Filed: Sep. 3, 1999

(51) Int. Cl.$^7$ .................... A61K 31/58; C07J 43/00
(52) U.S. Cl. ............... 514/176; 540/107; 540/108; 514/176; 514/841; 514/843
(58) Field of Search ................. 540/107, 108; 514/176, 841, 843, 179

(56) References Cited

U.S. PATENT DOCUMENTS

| | | | |
|---|---|---|---|
| 4,954,490 A | 9/1990 | Cook et al. ............ 558/54 |
| 5,073,548 A | 12/1991 | Cook et al. ............ 552/520 |
| 5,952,319 A | 9/1999 | Cook et al. ............ 514/179 |
| 6,020,328 A | * 2/2000 | Cook et al. ............ 514/176 |
| 6,072,068 A | 6/2000 | Groen et al. ........... 514/176 |

OTHER PUBLICATIONS

T. Garcia et al. "Switching Aonistic, Antagonistic, and Mixed Transcriptional Responses to 11.beta.–Substituted Progestins by Mutation of the Progesterone Receptor", Molecular Endocrinology, vol. 6, No. 12, 1992, pp. 2071–2078.

Chemical Abstracts, vol. 109, No. 15, Oct 10, 1988, Columbus, Ohio, US, Abstract No. 122708b, N. Tarawaka et al. "RU 486, a progestin antagonist, binds to progesterone receptors in a human endometrial cancer cell line and reverse the growth inhibition by progestins" p. 86.

H. J. Kloosterboer et al. "Screening of anti–progestagens by receptor studies and bioassays", J. Steroid Biochem., vol. 31, No. 4B, 1988, pp. 567–571.

C.E. Cook et al. "Reversal of activity profile in analogs of the antiprogestin RU 486: Effect of a 16.alpha.–substituent on progestational (agonist) activity" Life Sciences vol. 52, No. 2, 1993, pp. 155–162.

B.L. Wagner et al. 16.alpha.–Substituted analogs of the antiprogestin RU486 induce a unique conformation in the huyman progesterone receptor resulting in mixed agonist activity:, Proc. Natl. Acad. Sci. USA, vol. 93, 1996, pp. 8739–8744.

* cited by examiner

*Primary Examiner*—Sabiha Qazi
(74) *Attorney, Agent, or Firm*—Oblon, Spivak, McClelland, Maier & Neustadt, P.C.

(57) ABSTRACT

The invention is directed to a novel class of 17β-acyl-17α-propynyl steroids which exhibit potent antiprogestational activity.

13 Claims, No Drawings ns of the Invention

17β-ACYL-17α-PROPYNYL-11β-(CYCLIC AMINO) ARYL STEROIDS AND THEIR DERIVATIVES HAVING ANTAGONIST HORMONAL PROPERTIES

BACKGROUND OF THE INVENTION

1. Field of the Invention

This invention relates to a novel class of 17β-acyl-17α-propynyl-11β-(cyclic amino)aryl steroids which are believed to bind to the progestin receptor and which exhibit potent antiprogestational activity. Such compounds are useful for treatment of fibroids, endometriosis, and certain tumors, in causing cervical ripening prior to delivery, in hormone replacement therapy and in control of fertility and reproduction.

2. Discussion of the Background

Progesterone plays a major role in reproductive health and function. Its effects on, for example, the uterus, breast, cervix and hypothalamic-pituitary unit are well established. It also has extra-reproductive activities that are less well studied, such as effects on the brain, the immune system, the vascular endothelial system and on lipid metabolism. Given this wide array of effects, it is apparent that compounds which mimic some of the effects of progesterone (agonists), antagonize these effects (antagonists) or exhibit mixed effects (partial agonists or mixed agonist/antagonist) can be useful in treating a variety of disease states and conditions.

Steroid hormones exert their effects, in-part, by binding to intracellular receptors. Compounds that bind to the appropriate receptors and are antagonists or partial agonists of the estrogenic and androgenic hormones have long been known, but it was not until around 1982 that the discovery of compounds that bind to the progesterone receptor and antagonize the effects of progesterone was announced. Since then, a number of such compounds have been reported in the scientific and patent literature an humans have been studied. Although compounds such as estrogens and certain enzyme inhibitors can prevent the physiological effects of endogenous progesterone, in this discussion "antiprogestin" is confined to those compounds that bind to the progestin receptor.

Information indicating that antiprogestins would be effective in a number of medical conditions is now available. This information has been summarized in a report from the Institute of Medicine (Donaldson, Molly S.; Dorflinger, L.; Brown, Sarah S.; Benet, Leslie Z., Editors, *Clinical Applications of Mifepristone* (RU 486) *and Other Antiprogestins*, Committee on Antiprogestins: Assessing the Science, Institute of Medicine, National Academy Press, 1993). In view of the pivotal role that progesterone plays in reproduction, it is not surprising that antiprogestins could play a part in fertility control, including contraception (long-term and emergency or post-coital), menses induction and medical termination of pregnancy, but there are many other potential uses that have been supported by small clinical or preclinical studies. Among these are the following:

1. Labor and delivery—antiprogestins may be used for cervical ripening prior to labor induction such as at term or when labor must be induced due to fetal death. They may also be used to help induce labor in term or post-term pregnancies.
2. Treatment of uterine leiomyomas (fibroids)—these non-malignant tumors may affect up to 20% of women over 30 years old and are one of the most common reasons for surgery in women during their reproductive years. Hysterectomy, the common treatment for persistent symptoms, of course results in sterility.
3. Treatment of endometriosis—this common (5 to 15% incidence, much larger in infertile women) and often painful condition is now treated with drugs such as danazol or gonadotrophin-releasing hormone analogs that have significant side-effects, or must be dealt with surgically.
4. Hormone replacement therapy, where they may be given to interupt or curtail the activity of progestins.
5. Cancers, particularly breast cancers—the presence of progestin receptors in many breast cancers has suggested the use of antiprogestins in treating metastatic cancer or in prevention of recurrence or initial development of cancer.
6. Other tumors such as meningiomas—these brain membrane tumors, although non-malignant, result in death of the patient and nonsurgical treatments are lacking.
7. Male contraception—antiprogestins can interfere with sperm viability, although whether this is an antiprogestational effect or not is controversial, as it may relate to the antiglucocorticoid activity of such compounds.
8. Antiestrogenic effects—at least some antiprogestins oppose the action of estrogens in certain tests, but apparently through a mechanism that does not involve classical hormone receptors. This opens a variety of possibilities for their medical use.
9. Antiglucocorticoid effects—this is a common side-effect of antiprogestins, which can be useful in some instances, such as the treatment of Cushing's syndrome, and could play a role in immune disorders, for example. In other instances it is desirable to minimize such effects.

The effects and uses of progesterone agonists have been well documented. In addition, it has been recently shown that certain compounds structurally related to the known antiprogestins have strong agonist activity in certain biological systems (e.g., the classical progestin effects in the estrogen-primed immature rabbit uterus; cf. C. E. Cook et al., Life Sciences, 52, 155–162 (1993)). Such compounds are partial agonists in human cell-derived receptor systems, where they bind to a site distinct from both the progestin and antiprogestin sites (Wagner et al., Proc. Nat. Acad. Sci., 93, 8739–8744 (1996)). Thus the general class of antiprogestins can have subclasses, which may vary in their clinical profiles.

Generally antiprogestational activity has been associated with the presence of an 11β-aryl substituent on the steroid nucleus, together with a $\Delta^{4,9}$-3-ketone or $\Delta^4$-3-ketone moiety. However, it has been shown that substituents on the D-ring of the steroid can have a marked influence on the biological profile of these compounds (see above). The earliest antiprogestins were substituted with a 17β-hydroxyl group and various 17α-substituents. (See for example, Teutsch, Jean G.; Costerousse, Germain; Philibert, Daniel, and Deraedt, Roger. Novel steroids. U.S. Pat. No. 4,386,085. 1983; Philibert, Daniel; Teutsch, Jean G.; Costerousse, Germain, and Deraedt, Roger. 3-Keto-19-nor-Δ-4,9-steroids. U.S. Pat No. 4,477,445. 1983; Teutsch, Jean G.; Pantin, Germain; Costerousse, Saint-Maurice; Daniel Philibert; La Varenne Saint Hilaire; Roger Deraedt, inventors. Steroid derivatives. Roussel Uclaf, assignee. U.S. Pat No. 4,447,424. 1984; Cook, C. Edgar; Tallent, C. Ray; Reel, Jerry R., and Wani, Mansukh C. 17α-(Substituted-methyl)-17β-hydroxy/esterified hydroxy steroids and pharmaceutical compositions containing them. U.S. Pat No. 4,774,236 (1988) and U.S. Pat . No. 4,861,763 (1989)). Then it was discovered that a 17β-acetyl, 17α-acyloxy group could also generate antiprogestational effects (Cook, C. Edgar; Lee, Y.-W.; Reel, Jerry R.; Wani, Mansukh C., Rector, Douglas. 11β-Substituted Progesterone Analogs. U.S. Pat. No. 4,954, 490 (1990) and U.S. Pat. No. 5,073,548 (1991)), and various permutations of these findings have been made as well. However, introduction of a 16α-ethyl group or a hydrogen substituent at the 17α-position in the 17β-acyl series of compounds leads to agonist or partial agonist activity (C. E. Cook et al., Life Sciences, 52, 155–162 (1993)). Thus changes in the D-ring of the steroid result in a wide variety of effects on the biological activity.

Cook et al. U.S. Pat. No. 5,073,548 report 17α-alkynyl-11β-(substituted phenyl)-19-norpregna-4,9-diene-3,20-dione compounds but fail to exemplify 17β-acyl-17α-propyn-1-yl compounds.

Cook et al., in co-pending U.S. Ser. No. 09/035,949, filed on Mar. 16, 1998, report 17β-acyl-11β-(cyclic amino)phenyl steroids.

Cook et al., in co-pending U.S. Ser. No. 09/205,395, filed on Dec. 4, 1998, report 17β-acyl-17α-propynyl-11β-(dialkylamino)phenyl steroids, and an improved antiprogestin activity for compound bearing the 17α-propynyl group.

In spite of the clinical promise of antiprogestins, as of Nov. 1, 1998, there were no antiprogestin drugs marketed in the United States or many other countries. Only one antiprogestin drug is approved and available for clinical use anywhere in the world and that drug, mifepristone, is mainly used for medical termination of pregnancy. A number of factors are the cause of this situation, but certainly a need exists for new antiprogestational drugs that can be used for the conditions described above.

It is therefore the purpose of the present invention to provide novel and potent progestin antagonists (antiprogestins) and mixed or partial progestin agonists, and to provide methods for their medical use in mammals, including humans.

SUMMARY OF THE INVENTION

This invention provides a group of novel 17β-acyl-17α-propynyl-11β-(cyclic amino)aryl steroids, which are characterized by 11β-(4-cyclic amino substituted aryl) substitution.

According to one embodiment of the present invention is a hormonal or antihormonal steroid compound of structure I,

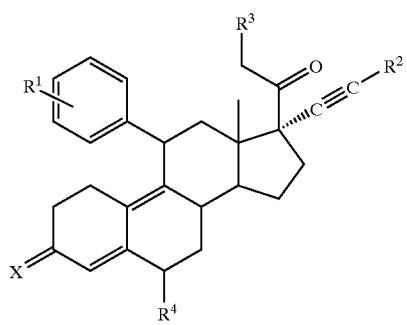

wherein $R^1$ is

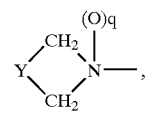

were q is 0 or 1, Y is —$(CH_2)_m$— where m is an integer of 0 to 5, or Y is —$(CH_2)_n$—Z—$(CH_2)_p$— where n is an integer of 0 through 2, p is an integer of 0 through 2 and Z is a heteroatom (optionally substituted where valency considerations permit) and where any of the $CH_2$ groups may be optionally substituted;

$R^2$ is $CH_3$—, $CF_3$— or $HOCH_2$—;
$R^3$ is H—, $CH_3$—, $CH_3O$—, $CH_3COO$— or halogen;
$R^4$ is H—, $CH_3$—, F— or Cl—; and
X is O, (H,H), NOH or $NOCH_3$,
and pharmaceutically acceptable salts thereof.

According to another embodiment of the present invention is a hormonal or anti-hormonal steroid compound of structure II

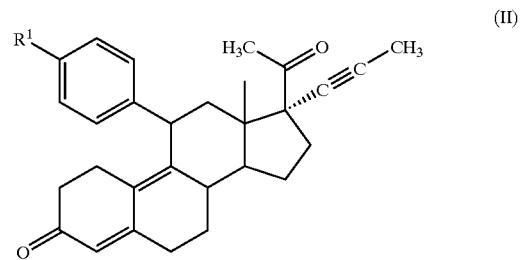

wherein $R^1$ is selected from the group consisting of N-piperidino, N-pyrrolidino, or N-morpholino.

According to another embodiment of the present invention is a hormonal or anti-hormonal steroid compound of structure III

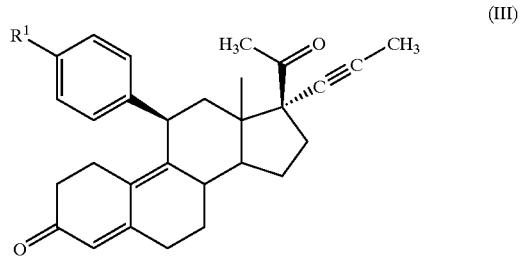

wherein $R^1$ is selected from the group consisting of N-piperidino, N-pyrrolidino, or N-morpholino.

These and other objects of the present invention are made possible by the discovery that 17β-acyl-17α-propynyl-11β-(4-cyclic amino)aryl) steroids exhibit exceptional antagonist hormonal activity.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein:

FIG. 1 depicts a reaction scheme to prepare 17β-acyl-17α-propynyl compounds according to the present invention.

DETAILED DESCRIPTION OF THE PREFERRED EMBODIMENTS

According to one embodiment of the present invention is a hormonal or antihormonal steroid compound of structure I,

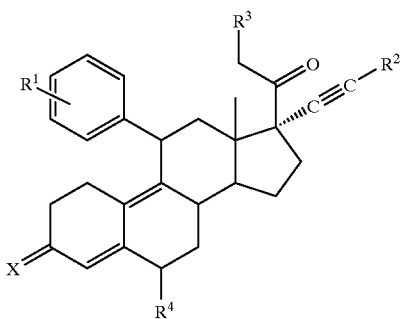

wherein

R¹ is

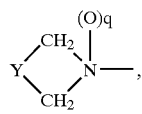

where q is 0 or 1, Y is —(CH$_2$)$_m$— where m is an integer of 0 to 5, or Y is —(CH$_2$)$_n$—Z—(CH$_2$)$_p$— where n is an integer of 0 through 2, p is an integer of 0 through 2 and Z is a heteroatom (optionally substituted where valency considerations permit) and where any of the CH$_2$ groups may be optionally substituted;

R² is CH$_3$—, CF$_3$— or HOCH$_2$—;

R³ is H—, CH$_3$—, CH$_3$O—, CH$_3$COO— or halogen;

R⁴ is H—, CH$_3$—, F— or Cl—; and

X is —O, (H,H), NOH or NOCH$_3$, and pharmaceutically acceptable salts thereof

According to another embodiment of the present invention is a hormonal or anti-hormonal steroid compound of structure II

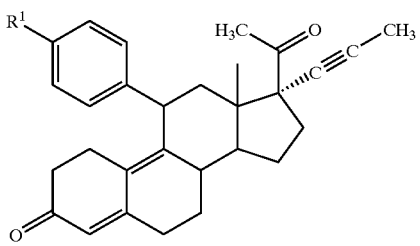

wherein R¹ is selected from the group consisting of N-piperidino, N-pyrrolidino, or N-morpholino.

According to another embodiment of the present invention is a hormonal or anti-hormonal steroid compound of structure III

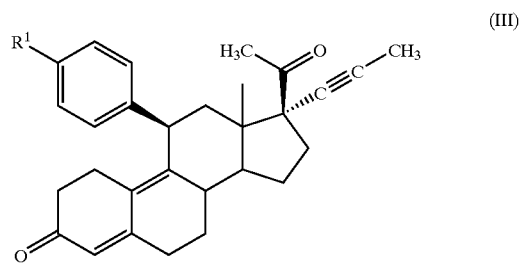

wherein R¹ is selected from the group consisting of N-piperidino, N-pyrrolidino, or N-morpholino.

The above-identified compounds of formula I specifically include compounds which are substituted on the A ring at the 3-position with two hydrogen atoms. These compounds are believed to undergo oxidation in vivo to the corresponding carbonyl compound.

The compounds of the present invention may also comprise a salt formed with the amine. Suitable pharmaceutically acceptable salts are known to those of ordinary skill in the art and comprise carboxylates, sulfates, phosphates and halides.

Within the context of the present invention, the group R⁴ in structure I may be in either the α or β stereochemical configuration.

Specific compounds according to the present invention are 11β-(4-N-morpholinophenyl)-17α-(1-propynyl)-19-norpregna-4,9-diene-3,20-dione;

11β-(4-N-morpholinophenyl)-17α-(3,3,3-trifluoropropyn-1-yl)-19-norpregna-4,9-diene-3,20-dione;

11β-(4-N-morpholinophenyl)-17α-(3-hydroxypropyn-1-yl)-19-norpregna-4,9-diene-3,20-dione;

11β-(4-N-morpholinophenyl)-21-methoxy-17α-(1-propynyl)-19-norpregna-4,9-diene-3,20-dione;

11β-(4-N-morpholinophenyl)-21-methoxy-17α-(3,3,3-trifluoropropyn-1-yl)-19-norpregna-4,9-diene-3,20-dione;

11β-(4-N-morpholinophenyl)-21-methoxy-17α-(3-hydroxypropyn-1-yl)-19-norpregna-4,9-diene-3,20-dione;

11β-(4-N-morpholinophenyl)-21-methoxy-3-oximino-17α-(1-propynyl)-19-norpregna-4,9-dien-20-one;

11β-(4-N-morpholinophenyl)-21-methoxy-3-oximino-17α-(3,3,3-trifluoropropyn-1-yl)-19-norpregna-4,9-dien-20-one;

11β-(4-N-morpholinophenyl)-21-methoxy-3-oximino-17α-(3-hydroxypropyn-1-yl)-19-norpregna-4,9-dien-20-one;

11β-(4-N-morpholinophenyl)-21-methoxy-6-fluoro-17α-(1-propynyl)-19-norpregna-4,9-diene-3,20-dione;

11β-(4-N-morpholinophenyl)-21-methoxy-6-fluoro-17α-(3,3,3-trifluoropropyn-1-yl)-19-norpregna-4,9-diene-3,20-dione;

11β-(4-N-morpholinophenyl)-21-methoxy-6-fluoro-17α-(3-hydroxypropyn-1-yl)-19-norpregna-4,9-diene-3,20-dione;

11β-(4-N-morpholinophenyl)-21-methoxy-6-fluoro-3-oximino-17α-(1-propynyl)-19-norpregna-4,9-dien-20-one;

11β-(4-N-morpholinophenyl)-21-methoxy-6-fluoro-3-oximino-17α-(3,3,3-trifluoropropyn-1-yl)-19-norpregna-4,9-dien-20-one;

11β-(4-N-morpholinophenyl)-21-methoxy-6-fluoro-3-oximino-17α-(3-hydroxypropyn-1-yl)-19-norpregna-4,9-dien-20-one;

11β-(4-N-morpholinophenyl)-21-methoxy-6-methyl-17α-(1-propynyl)-19-norpregna-4,9-diene-3,20-dione;

11β-(4-N-morpholinophenyl)-21-methoxy-6-methyl-17α-(3,3,3-trifluoropropyn-1-yl)-19-norpregna-4,9-diene-3,20-dione;

11β-(4-N-morpholinophenyl)-21-methoxy-6-methyl-17α-(3-hydroxypropyn-1-yl)-19-norpregna-4,9-diene-3,20-dione;

11β-(4-N-morpholinophenyl)-21-methoxy-6-methyl-3-oximino-17α-(1-propynyl)-19-norpregna-4,9-dien-20-one;

11β-(4-N-morpholinophenyl)-21-methoxy-6-methyl-3-oximino-17α-(3,3,3-trifluoropropyn-1-yl)-19-norpregna-4,9-dien-20-one;

11β-(4-N-morpholinophenyl)-21-methoxy-6-methyl-3-oximino-17α-(3-hydroxypropyn-1-yl)-19-norpregna-4,9-dien-20-one;

11β-(4-N-morpholinophenyl)-21-methyl-17α-(1-propynyl)-19-norpregna-4,9-diene-3,20-dione;

11β-(4-N-morpholinophenyl)-21-methyl-17α-(3,3,3-trifluoropropyn-1-yl)-19-norpregna-4,9-diene-3,20-dione;

11β-(4-N-morpholinophenyl)-21-methyl-17α-(3-hydroxypropyn-1-yl)-19-norpregna-4,9-diene-3,20-dione;

11β-(4-N-morpholinophenyl)-21-methyl-3-oximino-17α-(1-propynyl)-19-norpregna-4,9-dien-20-one;

11β-(4-N-morpholinophenyl)-21-methyl-3-oximino-17α-(3,3,3-trifluoropropyn-1-yl)-19-norpregna-4,9-dien-20-one;

11β-(4-N-morpholinophenyl)-21-methyl-3-oximino-17α-(3-hydroxypropyn-1-yl)-19-norpregna-4,9-dien-20-one;

11β-(4-N-morpholinophenyl)-21-methyl-6-fluoro-17α-(1-propynyl)-19-norpregna-4,9-diene-3,20-dione;

11β-(4-N-morpholinophenyl)-21-methyl-6-fluoro-17α-(3,3,3-trifluoropropyn-1-yl)-19-norpregna-4,9-diene-3,20-dione;

11β-(4-N-morpholinophenyl)-21-methyl-6-fluoro-17α-(3-hydroxypropyn-1-yl)-19-norpregna-4,9-diene-3,20-dione;

11β-(4-N-morpholinophenyl)-21-methyl-6-fluoro-3-oximino-17α-(1-propynyl)-19-norpregna-4,9-dien-20-one;

11β-(4-N-morpholinophenyl)-21-methyl-6-fluoro-3-oximino-17α-(3,3,3-trifluoropropyn-1-yl)-19-norpregna-4,9-dien-20-one;

11β-(4-N-morpholinophenyl)-6,21-methyl-6-fluoro-3-oximino-17α-(3-hydroxypropyn-1-yl)-19-norpregna-4,9-dien-20-one;

11β-(4-N-morpholinophenyl)-6,21-dimethyl-17-α-(1-propynyl)-19-norpregna-4,9-diene-3,20dione;

11β-(4-N-morpholinophenyl)-6,21-dimethyl-17α-(3,3,3-trifluoropropyn-1-yl)-19-norpregna-4,9-diene-3,20-dione;

11β-(4-N-morpholinophenyl)-6,21-dimethyl-17α-(3-hydroxypropyn-1-yl)-19-norpregna-4,9-diene-3,20-dione;

11β-(4-N-morpholinophenyl)-6,21-dimethyl-3-oximino-17α-(1-propynyl)-19-norpregna-4,9-dien-20-one;

11β-(4-N-morpholinophenyl)-6,21-dimethyl-3-oximino-17-α-(3,3,3-trifluoropropyn-1-yl)-19-norpregna-4,9-dien-20-one;

11β-(4-N-morpholinophenyl)-6,21-dimethyl-3-oximino-17α-(3-hydroxypropyn-1-yl)-19-norpregna-4,9-dien-20-one;

11β-(4-(N-morpholino)phenyl)-3-oximino-17α-(1-propynyl)-19-norpregna-4,9-dien-20-one;

11β-(4-(N-morpholino)phenyl)-3-oximino-17α-(3,3,3-trifluoropropyn-1-yl)-19-norpregna-4,9-dien-20-one;

11β-(4-(N-morpholino)phenyl)-3-oximino-17α-(3-hydroxypropyn-1-yl)-19-norpregna-4,9-dien-20-one;

11β-(4-(N-morpholino)phenyl)-6-fluoro-17α-(1-propynyl)-19-norpregna-4,9-diene-3,20-dione;

11β-(4-(N-morpholino)phenyl)-6-fluoro-17α-(3,3,3-trifluoropropyn-1-yl)-19-norpregna-4,9-diene-3,20-dione;

11β-(4-(N-morpholino)phenyl)-6-fluoro-17α-(3-hydroxypropyn-1-yl)-19-norpregna-4,9-diene-3,20-dione;

11β-(4-(N-morpholino)phenyl)-6-fluoro-3-oximino-17α-(1-propynyl)-19-norpregna-4,9-dien-20-one;

11β-(4-(N-morpholino)phenyl)-6-fluoro-3-oximino-17α-(3,3,3-trifluoropropyn-1-yl)-19-norpregna-4,9-dien-20-one;

11β-(4-(N-morpholino)phenyl)-6-fluoro-3-oximino-17α-(3-hydroxypropyn-1-yl)-19-norpregna-4,9-dien-20-one;

11β-(4-(N-morpholino)phenyl)-6-methyl-17α-(1-propynyl)-19-norpregna-4,9-diene-3,20-dione;

11β-(4-(N-morpholino)phenyl)-6-methyl-17α-(3,3,3-trifluoropropyn-1-yl)-19-norpregna-4,9-diene-3,20-dione;

11β-(4-(N-morpholino)phenyl)-6-methyl-17α-(3-hydroxypropyn-1-yl)-19-norpregna-4,9-diene-3,20-dione;

11β-(4-(N-morpholino)phenyl)-6-methyl-3-oximino-17α-(1-propynyl)-19-norpregna-4,9-dien-20-one;

11β-(4-(N-morpholino)phenyl)-6-methyl-3-oximino-17α-(3,3,3-trifluoropropyn-1-yl)-19-norpregna-4,9-dien-20-one;

11β-(4-(N-morpholino)phenyl)-6-methyl-3-oximino-17α-(3-hydroxypropyn-1-yl)-19-norpregna-4,9-dien-20-one;

11β-[4-(N-piperidino)phenyl]-17α-(1-propynyl)-19-norpregna-4,9-diene-3,20-dione;

11β-[4-(N-piperidino)phenyl]-17α-(3,3,3-trifluoropropyn-1-yl)-19-norpregna-4,9-diene-3,20-dione;

11β-[4-(N-piperidino)phenyl]-17-(3-hydroxypropyn-1-yl)-19-norpregna-4,9-diene-3,20-dione;

11β-[4-(N-piperidino)phenyl]-21-methoxy-17α-(1-propynyl)-19-norpregna-4,9-diene-3,20-dione;

11β-[4-(N-piperidino)phenyl]-21-methoxy-17α-(3,3,3-trifluoropropyn-1-yl)-19-norpregna-4,9-diene-3,20-dione;

11β-[4-(N-piperidino)phenyl]-21-methoxy-17α-(3-hydroxypropyn-1-yl)-19-norpregna-4,9-diene-3,20-dione;

11β-[4-(N-piperidino)phenyl]-21-methoxy-3-oximino-17α-(1-propynyl)-19-norpregna-4,9dien-20-one;

11β-[4-(N-piperidino)phenyl]-21-methoxy-3-oximino-17α-(3,3,3-trifluoropropyn-1-yl)-19-norpregna-4,9-dien-20-one;

11β-[4-(N-piperidino)phenyl]-21-methoxy-3-oximino-17α-(3-hydroxypropyn-1-yl)-19-norpregna-4,9-dien-20-one;

11β-[4-(N-piperidino)phenyl]-21-methoxy-6-fluoro-17α-(1-propynyl)-19-norpregna-4,9diene-3,20-dione;

11β-[4-(N-piperidino)phenyl]-21-methoxy-6-fluoro-17α-(3,3,3-trifluoropropyn-1-yl)-19-norpregna-4,9-diene-3,20-dione;

11β-[4-(N-piperidino)phenyl]-21-methoxy-6-fluoro-17α-(3-hydroxypropyn-1-yl)-19-norpregna-4,9-diene-3,20-dione;

11β-[4-(N-piperidino)phenyl]-21-methoxy-6-fluoro-3-oximino-17α-(1-propynyl)-19-norpregna-4,9-dien-20-one;

11β-[4-(N-piperidino)phenyl]-21-methoxy-6-fluoro-3-oximino-17α-(3,3,3-trifluoropropyn-1-yl)-19-norpregna-4,9-dien-20-one;

11β-[4-(N-piperidino)phenyl]-21-methoxy-6-fluoro-3-oximino-17α-(3-hydroxypropyn-1-19-norpregna-4,9-dien-20-one;

11β-[4-(N-piperidino)phenyl]-21-methoxy-6-methyl-17α-(1-propynyl)-19-norpregna-4,9-diene-3,20-dione;

11β-[4-(N-piperidino)phenyl]-21-methoxy-6-methyl-17α-(3,3,3-trifluoropropyn-1-yl)-19-norpregna-4,9-diene-3,20-dione;

11β-[4-(N-piperidino)phenyl]-21-methoxy-6-methyl-17α-(3-hydroxypropyn-1-yl)-19-norpregna-4,9-diene-3,20-dione;

11β-[4-(N-piperidino)phenyl]-21-methoxy-6-methyl-3-oximino-17α-(1-propynyl)-19-norpregna-4,9-dien-20-one;

11β-[4-(N-piperidino)phenyl]-21-methoxy-6-methyl-3-oximino-17α-(3,3,3-trifluoropropyn-1-yl)-19-norpregna-4,9-dien-20-one;

11β-[4-(N-piperidino)phenyl]-21-methoxy-6-methyl-3-oximino-17α-(3-hydroxypropyn-1-yl)-19-norpregna-4,9-dien-20-one;

11β-[4-(N-piperidino)phenyl]-21-methyl-17α-(1-propynyl)-19-norpregna-4,9-diene-3,20-dione;

11β-[4-(N-piperidino)phenyl]-21-methyl-17α-(3,3,3-trifluoropropyn-1-yl)-19-norpregnad-4,9-diene-3,20-dione;

11β-[4-(N-piperidino)phenyl]-21-methyl-17α-(3-hydroxypropyn-1-yl)-19-norpregna-4,9-diene-3,20-dione;

11β-[4-(N-piperidino)phenyl]-21-methyl-3-oximino-17α-(1-propynyl)-19-norpregna-4,9dien-20-one;

11β-[4-(N-piperidino)phenyl]-21-methyl-3-oximino-17α-(3,3,3-trifluoropropyn-1-yl)-19norpregna-4,9-dien-20-one;

11β-[4-(N-piperidino)phenyl]-21-methyl-3-oximino-17α-(3-hydroxypropyn-1-yl)-19-norpregna-4,9-dien-20-one;

11β-[4-(N-piperidino)phenyl]-21-methyl-6-fluoro-17α-(1-propynyl)-19-norpregna-4,9-diene-3,20-dione;

11β-[4-(N-piperidino)phenyl]-21-methyl-6-fluoro-17α-(3,3,3-trifluoropropyn-1-yl)-19norpregna-4,9-diene-3,20-dione;

11β-[4-(N-piperidino)phenyl]-21-methyl-6-fluoro-17α-(3-hydroxypropyn-1-yl)-19-norpregna-4,9-diene-3,20-dione;

11β-[4-(N-piperidino)phenyl]-21-methyl-6-fluoro-3-oximino-17α-(1-propynyl)-19-norpregna-4,9-dien-20-one;

11β-[4-(N-piperidino)phenyl]-21-methyl-6-fluoro-3-oximino-17α-(3,3,3-trifluoropropyn-1-yl)-19-norpregna-4,9-dien-20-one;

11β-[4-(N-piperidino)phenyl]-21-methyl-6-fluoro-3-oximino-17α-(3-hydroxypropyn-1-yl)-19-norpregna-4,9-dien-20-one;

11β-[4-(N-piperidino)phenyl]-6,21-dimethyl-17α-(1-propynyl)-19-norpregna-4,9-diene-3,20-dione;

11β-[4-(N-piperidino)phenyl]-6,21-dimethyl-17α-(3,3,3-trifluoropropyn-1-yl)-19-norpregna-4,9-diene-3,20-dione;

11β-[4-(N-piperidino)phenyl]-6,21-dimethyl-17α-(3-hydroxypropyn-1-yl)-19-norpregna-4,9-diene-3,20-dione;

11β-[4-(N-piperidino)phenyl]-6,21-dimethyl-3-oximino-17α-(1-propynyl)-19-norpregna-4,9-dien-20-one;

11β-[4-(N-piperidino)phenyl]-6,21-dimethyl-3-oximino-17α-(3,3,3-trifluoropropyn-1-yl)-19-norpregna-4,9-dien-20-one;

11β-[4-(N-piperidino)phenyl]-6,21-dimethyl-3-oximino-17α-(3-hydroxypropyn-1-yl)-19-norpregna-4,9-dien-20-one;

11β-[4-(N-piperidino)phenyl]-3-oximino-17α-(1-propynyl)-19-norpregna-4,9-dien-20-one;

11β-[4-(N-piperidino)phenyl]-3-oximino-17α-(3,3,3-trifluoropropyn-1-yl)-19-norpregna-4,9-dien-20-one;

11β-[4-(N-piperidino)phenyl]-3-oximino-17α-(3-hydroxypropyn-1-yl)-19-norpregna-4,9-dien-20-one;

11β-[4-(N-piperidino)phenyl]-6-fluoro-17α-(1-propynyl)-19-norpregna-4,9-diene-3,20-dione;

11β-[4-(N-piperidino)phenyl]-6-fluoro-17α-(3,3,3-trifluoropropyn-1-yl)-19-norpregna-4,9-diene-3,20-dione;

11β-[4-(N-piperidino)phenyl]-6-fluoro-17α-(3-hydroxypropyn-1-yl)-19-norpregna-4,9-diene-3,20-dione;

11β-[4-(N-piperidino)phenyl]-6-fluoro-3-oximino-17α-(1-propynyl)-19-norpregna-4,9-dien-20-one;

11β-[4-(N-piperidino)phenyl]-6-fluoro-3-oximino-17α-(3,3,3-trifluoropropyn-1-yl)-19-norpregna-4,9-dien-20-one;

11β-[4-(N-piperidino)phenyl]-6-fluoro-3-oximino-17α-(3-hydroxypropyn-1-yl)-19-norpregna-4,9-dien-20-one;

11β-[4-(N-piperidino)phenyl]-6-methyl-17α-(1-propynyl)-19-norpregna-4,9-diene-3,20-dione;

11β-[4-(N-piperidino)phenyl]-6-methyl-17α-(3,3,3-trifluoropropyn-1-yl)-19-norpregna-4,9-diene-3,20-dione;

11β-[4-(N-piperidino)phenyl]-6-methyl-17α-(3-hydroxypropyn-1-yl)-19-norpregna-4,9-diene-3,20-dione;

11β-[4-(N-piperidino)phenyl]-6-methyl-3-oximino-17α-(1-propynyl)-19-norpregna-4,9-dien-20-one;

11β-[4-(N-piperidino)phenyl]-6-methyl-3-oximino-17α-(3,3,3-trifluoropropyn-1-yl)-19-norpregna-4,9-dien-20-one;

11β-[4-(N-piperidino)phenyl]-6-methyl-3-oximino-17α-(3-hydroxypropyn-1-yl)-19-norpregna-4,9-dien-20-one;

11β-[4-(N-pyrrolidino)phenyl]-17α-(1-propynyl)-19-norpregna-4,9-diene-3,20-dione;

11β-[4-(N-pyrrolidino)phenyl]-17α-(3,3,3-trifluoropropyn-1-yl)-19-norpregna-4,9-diene-3,20-dione;

11β-[4-(N-pyrrolidino)phenyl]-17α-(3-hydroxypropyn-1-yl)-19-norpregna-4,9-diene-3,20-dione;

11β-[4-(N-pyrrolidino)phenyl]-21-methoxy-17α-(1-propynyl)-19-norpregna-4,9-diene-3,20-dione;

11β-[4-(N-pyrrolidino)phenyl]-21-methoxy-17α-(3,3,3-trifluoropropyn-1-yl)-19-norpregna-4,9-diene-3,20-dione;

11β-[4-(N-pyrrolidino)phenyl]-21-methoxy-17α-(3-hydroxypropyn-1-yl)-19-norpregna-4,9-diene-3,20-dione;

11β-[4-(N-pyrrolidino)phenyl]-21-methoxy-3-oximino-17α-(1-propynyl)-19-norpregna-4,9-dien-20-one;

11β-[4-(N-pyrrolidino)phenyl]-21-methoxy-3-oximino-17α-(3,3,3-trifluoropropyn-1-yl)-19-norpregna-4,9-dien-20-one;

11β-[4-(N-pyrrolidino)phenyl]-21-methoxy-3-oximino-17α-(3-hydroxypropyn-1-yl)-19-norpregna-4,9-dien-20-one;

11β-[4-(N-pyrrolidino)phenyl]-21-methoxy-6-fluoro-17α-(1-propynyl)-19-norpregna-4,9-diene-3,20-dione;

11β-[4-(N-pyrrolidino)phenyl]-21-methoxy-6-fluoro-17α-(3,3,3-trifluoropropyn-1-yl)-19-norpregna-4,9-diene-3,20-dione;

11β-[4-(N-pyrrolidino)phenyl]-21-methoxy-6-fluoro-17α-(3-hydroxypropyn-1-yl)-19-norpregna-4,9-diene-3,20-dione;

11β-[4-(N-pyrrolidino)phenyl]-21-methoxy-6-fluoro-3-oximino-17α-(1-propynyl)-19-norpregna-4,9-dien-20-one;

11β-[4-(N-pyrrolidino)phenyl]-21-methoxy-6-fluoro-3-oximino-17α-(3,3,3-trifluoropropyn-1-yl)-19-norpregna-4,9-dien-20-one;

11β-[4-(N-pyrrolidino)phenyl]-21-methoxy-6-fluoro-3-oximino-17α-(3-hydroxypropyn-1-yl)-19-norpregna-4,9-dien-20-one;

11β-[4-(N-pyrrolidino)phenyl]-21-methoxy-6-methyl-17α-(1-propynyl)-19-norpregna-4,9-diene-3,20-dione;

11β-[4-(N-pyrrolidino)phenyl]-21-methoxy-6-methyl-17α-(3,3,3-trifluoropropyn-1-yl)-19-norpregna-4,9-diene-3,20-dione;

11β-[4-(N-pyrrolidino)phenyl]-21-methoxy-6-methyl-17α-(3-hydroxypropyn-1-yl)-19-norpregna-4,9-diene-3,20-dione;

11β-[4-(N-pyrrolidino)phenyl]-21-methoxy-6-methyl-3-oximino-17α-(1-propynyl)-19-norpregna-4,9-dien-20-one;

11β-[4-(N-pyrrolidino)phenyl]-21-methoxy-6-methyl-3-oximino-17α-(3,3,3-trifluoropropyn-1-yl)-19-norpregna-4,9-dien-20-one;

11β-[4-(N-pyrrolidino)phenyl]-21-methoxy-6-methyl-3-oximino-17α-(3-hydroxypropyn-1-yl)-19-norpregna-4,9-dien-20-one;

11β-[4-(N-pyrrolidino)phenyl]-21-methyl-17α-(1-propynyl)-19-norpregna-4,9-diene-3,20-dione;

11β-[4-(N-pyrrolidino)phenyl]-21-methyl-17α-(3,3,3-trifluoropropyn-1-yl)-19-norpregna-4,9-diene-3,20-dione;

11β-[4-(N-pyrrolidino)phenyl]-21-methyl-17α-(3-hydroxypropyn-1-yl)-19-norpregna-4,9-diene-3,20-dione;

11β-[4-(N-pyrrolidino)phenyl]-21-methyl-3-oximino-17α-(1-propynyl)-19-norpregna-4,9-dien-20-one;

11β-[4-(N-pyrrolidino)phenyl]-21-methyl-3-oximino-17α-(3,3,3-trifluoropropyn-1-yl)-19-norpregna-4,9-dien-20-one;

11β-[4-(N-pyrrolidino)phenyl]-21-methyl-3-oximino-17α-(3-hydroxypropyn-1-yl)-19-norpregna-4,9-dien-20-one;

11β-[4-(N-pyrrolidino)phenyl]-21-methyl-6-fluoro-17α-(1-propynyl)-19-norpregna-4,9-diene-3,20-dione;

11β-[4-(N-pyrrolidino)phenyl]-21-methyl-6-fluoro-17α-(3,3,3-trifluoropropyn-1-yl)-19-norpregna-4,9-diene-3,20-dione;

11β-[4-(N-pyrrolidino)phenyl]-21-methyl-6-fluoro-17α-(3-hydroxypropyn-1-yl)-19-norpregna-4,9-diene-3,20-dione;

11β-[4-(N-pyrrolidino)phenyl]-21-methyl-6-fluoro-3-oximino-17α-(1-propynyl)-19-norpregna-4,9-dien-20-one;

11β-[4-(N-pyrrolidino)phenyl]-21-methyl-6-fluoro-3-oximino-17α-(3,3,3-trifluoropropyn-1-yl)-19-norpregna-4,9-dien-20-one;

11β-[4-(N-pyrrolidino)phenyl]-21-methyl-6-fluoro-3-oximino-17α-(3-hydroxypropyn-1-yl)-19-norpregna-4,9-dien-20-one;

11β-[4-(N-pyrrolidino)phenyl]-6,21-dimethyl-17α-(1-propynyl)-19-norpregna-4,9-diene-3,20-dione;

11β-[4-(N-pyrrolidino)phenyl]-6,21-dimethyl-17α-(3,3,3-trifluoropropyn-1-yl)-19-norpregna-4,9-diene-3,20-dione;

11β-[4-(N-pyrrolidino)phenyl]-6,21-dimethyl-17α-(3-hydroxypropyn-1-yl)-19-norpregna-4,9-diene-3,20-dione;

11β-[4-(N-pyrrolidino)phenyl]-6,21-dimethyl-3-oximino-17α-(1-propynyl)-19-norpregna-4,9-dien-20-one;

11β-[4-(N-pyrrolidino)phenyl]-6,21-dimethyl-3-oximino-17α-(3,3,3-trifluoropropyn-1-yl)-19-norpregna-4,9-dien-20-one;

11β-[4-(N-pyrrolidino)phenyl]-6,21-dimethyl-3-oximino-17α-(3-hydroxypropyn-1-yl)-19-norpregna-4,9-dien-20-one;

11β-[4-(N-pyrrolidino)phenyl]-3-oximino-17α-(1-propynyl)-19-norpregna-4,9-dien-20-one;

11β-[4-(N-pyrrolidino)phenyl]-3-oximino-17α-(3,3,3-trifluoropropyn-1-yl)-19-norpregna-4,9-dien-20-one;

11β-[4-(N-pyrrolidino)phenyl]-3-oximino-17α-(3-hydroxypropyn-1-yl)-19-norpregna-4,9-dien-20-one;

11β-[4-(N-pyrrolidino)phenyl]-6-fluoro-17α-(1-propynyl)-19-norpregna-4,9-diene-3,20-dione;

11β-[4-(N-pyrrolidino)phenyl]-6-fluoro-17α-(3,3,3-trifluoropropyn-1-yl)-19-norpregna-4,9-diene-3,20-dione;

11β-[4-(N-pyrrolidino)phenyl]-6-fluoro-17α-(3-hydroxypropyn-1-yl)-19-norpregna-4,9-diene-3,20-dione;

11β-[4-(N-pyrrolidino)phenyl]-6-fluoro-3-oximino-17α-(1-propynyl)-19-norpregna-4,9-dien-20-one;

11β-[4-(N-pyrrolidino)phenyl]-6-fluoro-3-oximino-17α-(3,3,3-trifluoropropyn-1-yl)-19-norpregna-4,9-dien-20-one;

11β-[4-(N-pyrrolidino)phenyl]-6-fluoro-3-oximino-17α-(3-hydroxypropyn-1-yl)-19-norpregna-4,9-dien-20-one;

11β-[4-(N-pyrrolidino)phenyl]-6-methyl-17α-(1-propynyl)-19-norpregna-4,9-diene-3,20-dione;

11β-[4-(N-pyrrolidino)phenyl]-6-methyl-17α-(3,3,3-trifluoropropyn-1-yl)-19-norpregna-4,9-diene-3,20-dione;

11β-[4-(N-pyrrolidino)phenyl]-6-methyl-17α-(3-hydroxypropyn-1-yl)-19-norpregna-4,9-diene-3,20-dione;

11β-[4-(N-pyrrolidino)phenyl]-6-methyl-3-oximino-17α-(1-propynyl)-19-norpregna-4,9-dien-20-one;

11β-[4-(N-pyrrolidino)phenyl]-6-methyl-3-oximino-17α-(3,3,3-trifluoropropyn-1-yl)-19-norpregna-4,9-dien-20-one;

11β-[4-(N-pyrrolidino)phenyl]-6-methyl-3-oximino-17α-(3-hydroxypropyn-1-yl)-19-norpregna-4,9-dien-20-one;

21-acetoxy-11β-(4-(N-morpholino)phenyl)-17α-(1-propynyl)-19-norpregna-4,9-diene-3,20-dione;

21-acetoxy-11β(4-(N-morpholino)phenyl)-17α-(3,3,3-trifluoropropyn-1-yl)-19-norpregna-4,9-diene-3,20-dione;

21-acetoxy-11β-(4-(N-morpholino)phenyl)-17α-(3-hydroxypropyn-1-yl)-19-norpregna-4,9-diene-3,20-dione;

21-acetoxy-11β-(4-(N-morpholino)phenyl)-3-oximino-17α-(1-propynyl)-19-norpregna-4,9-dien-20-one;

21-acetoxy-11β-(4-(N-morpholino)phenyl)-3-oximino-17α-(3,3,3-trifluoropropyn-1-yl)-19-norpregna-4,9-dien-20-one;

21-acetoxy-11β-(4-(N-morpholino)phenyl)-3-oximino-17α-(3-hydroxypropyn-1-yl)-19-norpregna-4,9-dien-20-one;

21-acetoxy-11β-(4-(N-morpholino)phenyl)-6-fluoro-17α-(1-propynyl)-19-norpregna-4,9-diene-3,20-dione;

21-acetoxy-11β-(4-(N-morpholino)phenyl)-6-fluoro-17α-(3,3,3-trifluoropropyn-1-yl)-19-norpregna-4,9-diene-3,20-dione;

21-acetoxy-11β-(4-(N-morpholino)phenyl)-6-fluoro-17α-(3-hydroxypropyn-1-yl)-19-norpregna-4,9-diene-3,20-dione;

21-acetoxy-11β-(4-(N-morpholino)phenyl)-6-fluoro-3-oximino-17α-(1-propynyl)-19-norpregna-4,9-dien-20-one;

21-acetoxy-11β-(4-(N-morpholino)phenyl)-6-fluoro-3-oximino-17α-(3,3,3-trifluoropropyn-1-yl)-19-norpregna-4,9-dien-20-one;

21-acetoxy-11β-(4-(N-morpholino)phenyl)-6-fluoro-3-oximino-17α-(3-hydroxypropyn-1-yl)-19-norpregna-4,9-dien-20-one;

21-acetoxy-11β-(4-(N-morpholino)phenyl)-6-methyl-17α-(1-propynyl)-19-norpregna-4,9-diene-3,20-dione;

21-acetoxy-11β-(4-(N-morpholino)phenyl)-6-methyl-17α-(3,3,3-trifluoropropyn-1-yl)-19-norpregna-4,9-diene-3,20-dione;

21-acetoxy-11β-(4-(N-morpholino)phenyl)-6-methyl-17α-(3-hydroxypropyn-1-yl)-19-norpregna-4,9-diene-3,20-dione;

21-acetoxy-11β-(4-(N-morpholino)phenyl)-6-methyl-3-oximino-17α-(1-propynyl)-19-norpregna-4,9-dien-20-one;

21-acetoxy-11β-(4-(N-morpholino)phenyl)-6-methyl-3-oximino-17α-(3,3,3-trifluoropropyn-1-yl)-19-norpregna-4,9-dien-20-one;

21-acetoxy-11β-(4-(N-morpholino)phenyl)-6-methyl-3-oximino-17α-(3-hydroxypropyn-1-yl)-19-norpregna-4,9-dien-20-one;

21-acetoxy-11β-[4-(N-piperidino)phenyl]-17α-(1-propynyl)-19-norpregna-4,9-diene-3,20-dione;

21-acetoxy-11β-[4-(N-piperidino)phenyl]-17α-(3,3,3-trifluoropropyn-1-yl)-19-norpregna-4,9-diene-3,20-dione;

21-acetoxy-11β-[4-(N-piperidino)phenyl]-17α-(3-hydroxypropyn-1-yl)-19-norpregna-4,9-diene-3,20-dione;

21-acetoxy-11β-[4-(N-piperidino)phenyl]-3-oximino-17α-(1-propynyl)-19-norpregna-4,9-dien-20-one;

21-acetoxy-11β-[4-(N-piperidino)phenyl]-3-oximino-17α-(3,3,3-trifluoropropyn-1-yl)-19-norpregna-4,9-dien-20-one;

21-acetoxy-11β-[4-(N-piperidino)phenyl]-3-oximino-17α-(3-hydroxypropyn-1-yl)-19-norpregna-4,9-dien-20-one;

21-acetoxy-11β-[4-(N-piperidino)phenyl]-6-fluoro-17α-(1-propynyl)-19-norpregna-4,9-diene-3,20-dione;

21-acetoxy-1β-[4-(N-piperidino)phenyl]-6-fluoro-17α-(3,3,3-trifluoropropyn-1-yl)-19-norpregna-4,9-diene-3,20-dione;

21-acetoxy-11β-[4-(N-piperidino)phenyl]-6-fluoro-17α-(3-hydroxypropyn-1-yl)-19-norpregna-4,9-diene-3,20-dione;

21-acetoxy-11β-[4-(N-piperidino)phenyl]-6-fluoro-3-oximino-17α-(1-propynyl)-19-norpregna-4,9-dien-20-one;

21-acetoxy-11β-[4-(N-piperidino)phenyl]-6-fluoro-3-oximino-17α-(3,3,3-trifluoropropyn-1-yl)-19-norpregna-4,9-dien-20-one;

21-acetoxy-11β-[4-(N-piperidino)phenyl]-6-fluoro-3-oximino-17α-(3-hydroxypropyn-1-19-norpregna-4,9-dien-20-one;

21-acetoxy-11β-[4-(N-piperidino)phenyl]-6-methyl-17α-(1-propynyl)-19-norpregna-4,9-diene-3,20-dione;

21-acetoxy-11β-[4-(N-piperidino)phenyl]-6-methyl-17α-(3,3,3-trifluoropropyn-1-yl)-19-norpregna-4,9-diene-3,20-dione;

21-acetoxy-11-[4-(N-piperidino)phenyl]-6-methyl-17α-(3-hydroxypropyn-1-yl)-19-norpregna-4,9-diene-3,20-dione;

21-acetoxy-11β-[4-(N-piperidino)phenyl]-6-methyl-3-oximino-17α-(1-propynyl)-19-norpregna-4,9-dien-20-one;

21-acetoxy-11β-[4-(N-piperidino)phenyl]-6-methyl-3-oximino-17α-(3,3,3-trifluoropropyn-1-yl)-19-norpregna-4,9-dien-20-one;

21-acetoxy-11β-[4-(N-piperidino)phenyl]-6-methyl-3-oximino-17α-(3-hydroxypropyn-1-yl 19-norpregna-4,9-dien-20-one;

21-acetoxy-11β-[4-(N-pyrrolidino)phenyl]-17α-(1-propynyl)-19-norpregna-4,9-diene-3,20-dione;

21-acetoxy-11β-[4-(N-pyrrolidino)phenyl]-17α-(3,3,3-trifluoropropyn-1-yl)-19-norpregna-4,9-diene-3,20-dione;

21-acetoxy-11β-[4-(N-pyrrolidino)phenyl]-17α-(3-hydroxypropyn-1-yl)-19-norpregna-4,9-diene-3,20-dione;

21-acetoxy-11β-[4-(N-pyrrolidino)phenyl]-3-oximino-17α-(1-propynyl)-19-norpregna-4,9-dien-20-one;

21-acetoxy-11β-[4-(N-pyrrolidino)phenyl]-3-oximino-17α(3,3,3-trifluoropropyn-1-yl)-19-norpregna-4,9-dien-20-one;

21-acetoxy-11β-[4-(N-pyrrolidino)phenyl]-3-oximino-17α-(3-hydroxypropyn-1-yl)-19-norpregna-4,9-dien-20-one;

21-acetoxy-11-[4-(N-pyrrolidino)phenyl]-6-fluoro-17α-(1-propynyl)-19-norpregna-diene-3,20-dione;

21-acetoxy-11β-[4-(N-pyrrolidino)phenyl]-6-fluoro-17α-(3,3,3-trifluoropropyn-1-yl)-19-norpregna-4,9-diene-3,20-dione;

21-acetoxy-11β-[4-(N-pyrrolidino)phenyl]-6-fluoro-17α-(3-hydroxypropyn-1-yl)-19-norpregna-4,9-diene-3,20-dione;

21-acetoxy-11β-[4-(N-pyrrolidino)phenyl]-6-fluoro-3-oximino-17α-(1-propynyl)-19-norpregna-4,9-dien-20-one;

21-acetoxy-11β-[4-(N-pyrrolidino)phenyl]-6-fluoro-3-oximino-17α(3-hydroxypropyn-19-norpregna-4,9-dien-20-one;

21-acetoxy-11β-[4-(N-pyrrolidino)phenyl]-6-fluoro-3-oximino-17α-(3,3,3-trifluoropropyn-1-yl)-19-norpregna-4,9-dien-20-one;

21-acetoxy-11β-[4-(N-pyrrolidino)phenyl]-6-methyl-17α-(-1-propynyl)-19-norpregna-4,9-diene-3,20-dione; 21-acetoxy-11β-[4-(N-pyrrolidino)phenyl]-6-methyl-17α-(3,3,3-trifluoropropyn-1-yl)-19-norpregna-4,9-diene-3,20-dione;

21-acetoxy-11β-[4-(N-pyrrolidino)phenyl]-6-methyl-17α-(3-hydroxypropyn-1-yl)-19-norpregna-4,9-diene-3,20-dione;

21-acetoxy-11β-[4-(N-pyrrolidino)phenyl]-6-methyl-3-oximino-17α-(1-propynyl)-19-norpregna-4,9-dien-20-one; 21-acetoxy-11β-[4-(N-pyrrolidino)phenyl]-6-methyl-3-oximino-17α-(3-hydroxypropyn-1-yl)-19-norpregna-4,9-dien-20-one; and 21-acetoxy-11β-[4-(N-pyrrolidino)phenyl]-6-methyl-3-oximino-17α-(3,3,3-trifluoropropyn-1-yl)-19-norpregna-4,9-dien-20-one.

Compounds of the invention may be synthesized by conventional methods known to those of ordinary skill in the art, such as the scheme shown in FIG. 1. In FIG. 1, the group $R^1$, is illustrated as a (N-piperidino)phenyl group. However, analogous cyclic amino compounds may be synthesized by analogous methods.

Compounds of this invention may be made as exemplified by the synthesis of 11β-[4-(N-piperidino)phenyl]-17α-(1-propynyl)-19-norpregna-4,9-diene-3,20-dione (8, RT 041), as outlined in FIG. 1. The starting material for compound 1 (numbers refer to the compound numbers in the Figure), 17β-cyano-3,3-[1,2-ethanediylbis(oxy)]-17α-trimethylsilyloxyestra-5(10),9(11)-diene, may b obtained by conventional methods known to those of ordinary skill in the art, such as by the method described by V. Crocq, et al., Organic Process Research & Development, 1: 2–13 (1997). This compound is treated with methylmagnesium bromide to yield the keto compound 1, which is then converted to the acetoxy compound 2 with acetic acid/trifluoroacetic anhydride mixture. Reketalization of the dienone system of 2 with ethylene glycol in the presence of an acid catalyst yields 3, which is converted to the epoxide 4 by treatment with a peroxy acid or more preferably with hydrogen peroxide in the presence of a fluorinated ketone such as for example hexafluoroacetone. Treatment of the mixture of epoxides thus obtained (4 and its β-epimer) with a copper(I) salt (preferably CuI) and an aryl Grignard reagent [exemplified by 4-(N-piperidino)phenylmagnesium bromide] leads to the arylated intermediate 5. When this compound is treated with lithium in liquid ammonia, the resulting anion may be alkylated with propargyl bromide to yield the propargyl-substituted ketone intermediate 6. It has been discovered that the generation of the anion could be performed selectively, in the presence of groups potentially reducible by lithium/liquid ammonia, such as the aminoaryl group. The terminal triple bond of 6 may be rearranged to the internal position to give compound 7 by treatment with potassium t-butoxide in anhydrous dimethylsulfoxide. (For this reaction to occur rapidly and in good yield it is preferable that the dimethylsulfoxide be dry. Commercial anhydrous dimethylsulfoxide (DMSO) for laboratory use, which has been protected from moisture, is usually acceptable.) Acid hydrolysis and dehydration, such as for example with trifluoroacetic acid and water, leads to the propynyl compound 8 (RTI-6617-041).

Analogous procedures may be used to make other compounds of the invention as well as other 11β-aryl-17α-propynyl-19-norpregna-4,9-diene-3,20-diones, such as for example the acyclic aminoaryl compounds of U.S. application Ser. No. 09/205,395, filed with the U.S. patent office on Dec. 4, 1998, the relevant portion thereof being hereby incorporated by reference.

The synthesis of other 17α-propynyl compounds may be achieved by analogous procedures (see Examples).

Steroids having progestational, antiprogestational and/or antiglucocorticoid activity have use in the control of fertility in humans and non-human mammals such as primates, domestic pets and farm animals, and in the treatment of medical conditions in animals or humans in which these activities are beneficial. Thus they may be useful in the treatment of conditions such as fibroids, Cushing's syndrome, glaucoma, endometriosis, cervical ripening prior to delivery, hormone replacement therapy, premenstrual syndrome and cancer in addition to their use in the control of fertility and reproduction.

The compounds of the present invention may be administered by a variety of methods. Thus, those products of the invention that are active by the oral route may be administered in solutions, suspensions, emulsions, tablets, including sublingual and intrabuccal tablets, soft gelatin capsules, including solutions used in soft gelatin capsules, aqueous or oil suspensions, emulsions, pills, lozenges, troches, tablets, syrups or elixirs and the like. Products of the invention active on parenteral administration may be administered by depot injection, implants including Silastic™ and biodegradable implants, intramuscular and intravenous injections.

Compositions may be prepared according to any method known to the art for the manufacture of pharmaceutical compositions and such compositions may contain one or more agents selected from the group consisting of sweetening agents, flavoring agents, coloring agents and preserving agents. Tablets containing the active ingredient in admixture with nontoxic pharmaceutically acceptable excipients which are suitable for manufacture of tablets are acceptable. These excipients may be, for example, inert diluents, such as calcium carbonate, sodium carbonate, lactose, calcium phosphate or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may also be presented as hard gelatin capsules wherein the active ingredient is mixed with an inert solid diluent, for example calcium carbonate, calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl-ethyl cellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension may also contain one or more preservatives such as ethyl or n-propyl p-hydroxybenzoate, one or more coloring agents, one or more flavoring agents and one or more sweetening agents, such as sucrose, aspartame or saccharin. Ophthalmic formulations, as is known in the art, will be adjusted for osmotic pressure.

Oil suspensions may be formulated by suspending the active ingredient in a vegetable oil, such as arachis oil, olive oil, sesame oil or coconut oil, or in a mineral oil such as liquid paraffin. The oil suspensions may contain a thickening agent, such as beeswax, hard paraffin or cetyl alcohol. Sweetening agents may be added to provide a palatable oral preparation. These compositions may be preserved by the addition of an antioxidant such as ascorbic acid.

Dispersible powders and granules of the invention suitable for preparation of an aqueous suspension by the addition of water may be formulated from the active ingredients in admixture with a dispersing, suspending and/or wetting agent, and one or more preservatives. Suitable dispersing or wetting agents and suspending agents are exemplified by those disclosed above. Additional excipients, for example sweetening, flavoring and coloring agents, may also be present.

The pharmaceutical composition of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a nontoxic parenterally acceptable diluent or solvent, such as a solution of 1,3-butanediol.

Among the acceptable vehicles and solvents that may be employed are water and Ringer's solution, an isotonic sodium chloride. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables. Sterilization may be performed by conventional methods known to those of ordinary skill in the art such as by aseptic filtration, irradiation or terminal sterilization (e.g. autoclaving).

Aqueous formulations (i.e oil-in-water emulsions, syrups, elixers and injectable preparations) may be formulated to achieve the pH of optimum stability. The determination of the optimum pH may be performed by conventional methods known to those of ordinary skill in the art. Suitable buffers may also be used to maintain the pH of the formulation.

The compounds of this invention may also be administered in the form of suppositories for rectal administration of the drug. These compositions can be prepared by mixing the drug with a suitable nonirritating excipient which is solid at ordinary temperatures but liquid at the rectal temperatures and will therefore melt in the rectum to release the drug. Non-limiting examples of such materials are cocoa butter and polyethylene glycols.

They may also be administered by intranasal, intraocular, intravaginal, and intrarectal routes including suppositories, insufflation, powders and aerosol formulations.

Products of the invention which are preferably administered by the topical route may be administered as applicator sticks, solutions, suspensions, emulsions, gels, creams, ointments, pastes, jellies, paints, powders, and aerosols.

Products having anti-glucocorticoid activity are of particular value in pathological conditions characterized by excess endogenous glucocorticoid such as Cushing's syndrome, hirsutism and in particular when associated with the adrenogenital syndrome, ocular conditions associated with glucocorticoid excess such as glaucoma, stress symptoms associated with excess glucocorticoid secretion and the like.

Products having progestational activity are of particular value as progestational agents, ovulation inhibitors, menses regulators, contraceptive agents, agents for synchronization of fertile periods in cattle, and the like. When used for contraceptive purposes, they may conveniently be admixed with estrogenic agents, such as for example as ethynylestradiol or estradiol esters.

Products having anti-progestational activity are characterized by antagonizing the effects of progesterone. As such, they are of value in assisting in labor and delivery, in treatment of fibroids and endometriosis and in hormone replacement therapy.

The compounds of the invention may be used for control of fertility during the whole of the reproductive cycle. They are of particular value as postcoital contraceptives, for rendering the uterus inimical to implantation, and as "once a month" contraceptive agents. They may be used in conjunction with prostaglandins, oxytocics, estrogens and the like. In addition, a method of therapeutically adjusting the activity of progesterone may be practiced by administering compounds of the invention with one or more pharmacologically active compounds.

A further important utility for the products of the invention lies in their ability to slow down growth of hormone-dependent cancers. Such cancers include kidney, breast, endometrial, ovarian cancers, and prostate cancer which are characterized by possessing progesterone receptors and may be expected to respond to the products of this invention. Other utilities of anti-progestational agents include treatment of fibrocystic disease of the breast. Certain cancers and in particular melanomas and gliomas may respond favorably to corticoid/articorticoid therapy.

The compounds according to the present invention may be administered to any warm-blooded mammal such as humans, domestic pets, and farm animals. Domestic pets include dogs, cats, etc. Farm animals include cows, horses, pigs, sheep, goats, etc.

The amount of active ingredient that may be combined with a carrier material to produce a single dosage form will vary depending upon the disease treated, the mammalian species, and the particular mode of administration. A therapeutically effective amount may be determined by routine experimentation and by analogy from the amounts used to treat the same disease states with analogous steroid compounds. For example, a unit dose of the steroid may preferably contain between 0.1 milligram and 1 gram of the active ingredient. A more preferred unit dose is between 0.001 and 0.5 grams. For the specific treatment of endometriosis or fibroids an amount of 0.01 to 10 mg/kg of body weight, preferably from 0.1 to 3 mg/kg may be administered. Similar dosages may be used for the other therapeutic purposes of these compounds. Ordinarily the compounds may be administered daily 1 to 4 times per day, preferably 1 to 2 times per day, but for uses such as for example in hormone replacement therapy, they may be administered in a cyclophasic regimen. In any case the frequency and timing of dosage will depend upon factors such as the half-life of the specific compound in the body, the dosage formulation and the route of administration. It will be understood, however, that the specific dose level for any particular patient will depend on a variety of factors including the activity of the specific compound employed; the age, body weight, general health, sex and diet of the individual being treated; the time and route of administration; the rate of excretion; other drugs which have previously been administered; and the severity of the particular disease undergoing therapy, as is well understood by those of skill in the art.

Such compounds are useful in the treatment of endometriosis, uterine leiomyomas (fibroids) and certain cancers and tumors, in hormone replacement therapy as well as in the control of various steps in reproduction and fertility, such as contraception. A more detailed description of the potential uses of such compounds is given in Donaldson, Molly S.; Dorflinger, L.; Brown, Sarah S.; Benet, Leslie Z., Editors, *Clinical Applications of Mifepristone (RU 486) and Other Antiprogestins*, Committee on Antiprogestins: Assessing the Science, Institute of Medicine, National Academy Press, 1993. They are also useful as intermediates for the synthesis of other steroids.

General Methods. Unless otherwise stated, reagent-grade chemicals and solvents were obtained from commercial sources and were used without further purification. All moisture- and air-sensitive reactions and reagent transfers were carried out under dry nitrogen or argon. Thin layer chromatography (TLC) was performed on EM Science precoated silica gel 60 F-254 plates. Compounds were normally visualized by LTV light (254 nm) or para-anisaldehyde spray. Preparative column chromatography employed EM Science silica gel, 60Å (230–400 mesh). Solvent ratios given are volume:volume. Solutions were concentrated by use of a rotoevaporator under water aspirator pressure at ambient temperature. Melting points were taken on a Mel-Temp II and are uncorrected. Unless otherwise noted, $^1$H NMR spectra were obtained at 250 MHz on a Bruker AC 250 spectrometer in $CDCl_3$ as solvent with tetramethylsilane (TMS) as internal standard. Chemical shifts are reported in units of ppm downfield from TMS. Mass spectra were normally obtained by electron impact at 70 eV on a Hewlett Packard 5989A instrument. Elemental analyses were performed by Atlantic Microlab Inc., Atlanta, Ga.

3,3-[1,2-Ethanediylbis(oxy)]-17α-hydroxy-19-norpregna-5(10),9(11)-dien-20-one (1)

To a solution of 112.8 g (0.27 mol) of 17β-cyano-3,3-[1,2-ethanediylbis(oxy)]-17α-trimethylsilyloxyestra-5(10),9(11)-diene in 855 mL of anhydrous toluene and 255 mL of dry tetrahydroetran (THF) under argon was added 806 mL of methylmagnesium bromide (1.4 M in 3:1 toluene/THF, 1.13 mol) in one portion. The dark green solution was brought to reflux an d allowed to reflux for 16 h. The reaction mixture was allowed to cool to room temperature, and then was poured over 2.0 L of cold 10% aqueous $NH_4Cl$ solution. The organic phase was separated and the aqueous phase was extracted twice with toluene. The combined organic extracts were washed with HCl solution (1:99 concentrated aqueous HCl/water) until the aqueous phase was pH 5 and immediately washed with a 2.5% solution of $NaHCO_3$ until the aqueous phase remained basic. After washing with brine, the solution was dried over $MgSO_4$, filtered, evaporated, and dried to give a crude residue (55 g). Re-extraction of the washes yielded another 21 g. Purification by silica gel chromatography with isocratic elution (hexane: EtOAc: $CH_2Cl_2$, 31:8:1) afforded 45.1 g (46.7% yield) of 1 as a white solid. $^1$H NMR (250 MHz; $CDCl_3$) δ 5.57 (br s, 1, 11-H), 3.98 (s, 4, O—$CH_2$—$CH_2$—O), 2.83 (s, 1, —OH), 2.27 (s, 3,21-$CH_3$), 0.69 (s, 3, 18-$CH_3$).

17α-Acetoxy-19-norpregna-4,9-diene-3,20-dione (2)

To a 0° C. suspension of p-toluene sulfonic acid (57 g, 0.302 mol), and acetic acid (216 mL, 3.78 mol) in 450 mL of $CH_2Cl_2$ was added slowly, in portions, 534 mL (3.78 mol) of trifluoroacetic anhydride while maintaining a temperature of 0° C. After a clear solution resulted, a cold (0° C.) solution of 1 (50 g, 0.14 mol) in 300 mL of $CH_2Cl_2$ was added in on portion. The resulting yellow-brown solution was stirred at 0° C. for 10 min. The reaction mixture was poured over ice-water and basified with 2 L of saturated $K_2CO_3$ solution and additional solid $K_2CO_3$ to bring the pH to 9.0. The product was extracted with $CHCl_3$, dried over $Na_2SO_4$, filtered, evaporated, and dried to give 49.72 g (99% yield) of 2 as a light-yellow crystalline solid, used without further purification. $^1$H NMR (250 MHz; $CDCl_3$) δ 5.70 (br s, 1, 11-H), 2.12 (s, 3,21-Me), 2.08 (s, 3, 17-$OCOCH_3$), 0.80 (s, 3, 18-Me).

17α-Acetoxy-3,3-[1,2-ethanediylbis(oxy)]-19-norpregna-5(10),9(11)-dien-20-one (3)

A mixture of p-toluene sulfonic acid (1.33 g, 7.0 mmol), 115 mL (2.1 mol) of ethylene glycol, and 1.0 L of toluene was brought to reflux and 300 mL of toluene was distilled off. Compound 2 (49.72 g, 0.14 mol) in 250 mL of toluene was added, the resulting mixture was heated to reflux and 300 mL of toluene was distilled. The reaction mixture was poured over ice-water and neutralized with saturated $NaHCO_3$ solution. The product was extracted with $CH_2Cl_2$, dried over $Na_2SO_4$, filtered, evaporated, and dried to afford 54 g of 3, used without further purification. $^1$H NMR (250

MHz, CDCl$_3$) δ 5.57 (br s, 1, 11-H), 3.99 (s, 4, 3-ketal), 2.07 (s, 3, 21-Me), 2.06 (s, 3, 17-OCOCH$_3$), 0.62 (s, 3, 18-Me).

17α-Acetoxy-3,3-[1,2-ethanediylbis(oxy)]-5,10α-oxido-19-norpregn-9(11)-en-20-one (4)

Compound 3 (14.82 g, 37 mmol) was dissolved in CH$_2$Cl$_2$ (220 mL) and the solution was cooled to 0° C. in an ice bath. Solid Na$_2$HPO$_4$ (3.15 g, 22.24 mmol) was added and the mixture was stirred for 5 min. Hexafluoroacetone (3.1 mL, 22.24 mmol) and 50% H$_2$O$_2$ (5.3 mL, 91.9 mmol) were added and the reaction mixture was stirred and allowed to warm to room temperature overnight. The reaction was quenched with saturated NaHCO$_3$ solution and extracted three times with CH$_2$Cl$_2$. The organic layers were combined, washed with water and brine, and dried over Na$_2$SO$_4$. The solvent was removed in vacuo to yield 4 as a fluffy yellow solid (15.40 g) in quantitative yield. The crude product was a 4:1 ratio of α to β epoxide isomers. No further purification was performed.

17α-Acetoxy-3,3-[1,2-ethanediylbis(oxy)]-5α-hydroxy-11β-[4-(N-piperidino)phenyl]-19-norpregn-9-en-20-one (5)

A mixture of 4 (6.3 g, 15.13 mmol) and CuI (5.76 g, 30.25 mmol) in dry THF (115 mL) was stirred and cooled to 0° C. under argon. A freshly prepared Grignard solution, made from 1-bromo-4-(N-piperidino)benzene (14.55 g, 60.6 mmol) and Mg turnings (1.50 g, 61.70 mmol) in dry THF (130 mL), was added via cannula. The reaction was quenched after 10 min with saturated NH$_4$Cl and was stirred vigorously at room temperature for 30 min. The two layers were separated and the aqueous layer was extracted twice with a mixture of EtOAc and ether. The organic layers were combined, washed with saturated NH$_4$Cl solution, water and brine, and dried over Na$_2$SO$_4$. The solvent was removed in vacuo. Purification of the residue by column chromatography [SiO$_2$, 700 mL; 1:1 hexanes-EtOAc (1 L) increased gradually to 2:3 hexanes-EtOAc] afforded compound 5 (6.5 g) in 75% yield for the two steps. $^1$H NMR δ 7.02 (d, 2, J=8.5 Hz, ArH), 6.81 (d, 2, J=8.7 Hz, ArH), 4.46 (s, 1, C$_{5α}$OH), 4.29(d, 1, J=7.1 Hz, C$_{11α}$H), 3.98 (m, 4, ketal), 3.09 (m, 4, N(CH$_2$)$_2$), 2.11(s, 3, C$_{21}$H), 206 (s, 3, OAc), 027 (s, 3, C$_{18}$H).

3,3-[1,2-Ethanediylbis(oxy)]-5α-hydroxy-11β-[4-(N-piperidino)phenyl]-17α-(3-propynyl)-19-norpregn-9-en-20-one (6)

A 1 L 3-neck round bottom flask was charged with liquid NH$_3$ (250 mL) under an inert atmosphere at −78° C. Lithium wire (540 mg, 77.8 mmol) was added in small pieces, turning the reaction dark blue. The reaction was stirred at −78° C. for 30 min followed by addition of dry THF (40 mL). After 5 min, compound 5 (6.45 g, 11.2 mmol) in dry THF (110 mL) was added over 25 min. The reaction remained dark blue and was stirred at −78° C. for 90 min. Propargyl bromide in toluene (80% by wt, 24.5 mL, 220 mmol) was added, turning the reaction a creamy color. The mixture was stirred vigorously and allowed to slowly warm to room temperature overnight. The reaction was quenched with water (300 mL) and diluted with CH$_2$Cl$_2$. The two layers were separated and the aqueous layer was extracted twice with CH$_2$Cl$_2$. The organic layers were combined, then washed with saturated NH$_4$Cl solution and brine. The washed solution was dried over Na$_2$SO$_4$ and the solvent was removed in vacuo. The product was purified by flash column chromatography [SiO$_2$, 1400 mL; 3:2 hexanes-EtOAc (2.5 L) increased gradually to 1:1 hexanes-EtOAc] to afford compound 6 (4.96 g) in 79.5% yield. $^1$H NMR δ 7.03 (d, 2, J=8.6 Hz, ArH), 6.81 (d, 2, J=8.7 Hz, ArH), 4.39 (s, 1, C$_{5α}$OH), 4.24 (d, 1, J=6.4 Hz, C$_{11α}$H), 3.99 (m, 4, ketal), 3.10 (m, 4, N(CH$_2$)$_2$), 2.17 (s, 3, C$_{21}$H), 0.30 (s, 3, C$_{18}$ H).

3,3-[1,2-Ethanediylbis(oxy)]-5α-hydroxy-11β-[4-(N-piperidino)phenyl]-17α-(1-propynyl)-19-norpregn-9-en-20-one (7)

t-BuOK (820 mg, 7.3 mmol) dissolved in dry DMSO (16 mL) under Ar was cooled slightly in a cool water bath (about 10° C.). Compound 6 (3.7 g, 6.34 mmol) in dry DMSO (65 mL) was added, turning the reaction dark reddish-brown. After 10 min, the reaction was quenched with saturated NH$_4$Cl solution and diluted with EtOAc. After being stirred vigorously for 30 min the two layers were separated. The aqueous layer was extracted three times with EtOAc. The organic layers were combined and washed with saturated NH$_4$Cl solution, water and brine. The washed solution was dried over Na$_2$SO$_4$ and the solvent was removed in vacuo. No further purification was performed and the crude 7 was used in the next step. $_1$H NMR δ 7.04 (d, 2, J=8.6 Hz, ArH), 6.80 (d, 2, J 8.6 Hz, ArH), 4.43 (s, 1, C$_{5α}$OH), 4.11(d, 1, J=6.4 Hz, C$_{11α}$H), 3.97 (m, 4, ketal), 3.08 (m, 4, N(CH$_2$)$_2$), 2.25 (s, 3, C$_{21}$ H), 1.86 (s, 3, propynyl CH$_3$), 0.21 (s, 3, C$_{18}$ H).

11β-[4-(N-Piperidino)phenyl]-17α-(1-propynyl)-19-norpregna4,9-diene-3,20-dione (8, RTI-6617–041)

Crude 7 (assumed 6.34 mmol) was dissolved in CH$_2$Cl$_2$ (300 mL) and cooled under Ar to 0° C. Trifluoroacetic acid (7.5 mL) and water (6 mL) were added. After 40 min of stirring at 0° C., the reaction was quenched with saturated NaHCO$_3$ solution (100 mL) and allowed to warm to room temperature. The two layers were separated and the aqueous layer was extracted three times with CH$_2$Cl$_2$. The organic layers were combined, washed with water and brine, and dried over Na$_2$SO$_4$. The solvent was removed in vacuo, giving compound 8 in quantitative crude yield. Purification by column chromatography (5:4 hexanes-EtOAc) afforded compound 8 (1.96 g) in 60% yield for two steps. $^1$H NMR δ 7.01 (d, 2, J=8.6 Hz, ArH), 6.83 (d, 2, J=8.6 Hz, ArH), 5.77 (s, 1, C$_4$H), 4.39 (d, 1, J=6.9 Hz, C$_{11α}$H), 3.10 (m, 4, N(CH$_2$)$_2$), 2.29 (s, 3, C$_2$ H), 1.89 (s, 3, propynyl CH$_3$), 0.29 (s, 3, C$_{18}$ H).

This material was combined with a previous batch and further purified by column chromatography (SiO$_2$, 500 mL; 3:2 hexanes-EtOAc) to afford compound 8 (2.41 g) that was greater than 98% pure by analytical HPLC. (C-18 column, 9:1 MeOH—H$_2$O, 1 mL/min, t$_R$ 6.4 min. MS (El, m/z), 495 (M$^+$). Anal. Calcd. C$_{34}$H$_{41}$NO$_2$: C, 82.38; H, 8.34; N, 2.83. Found C, 82.09; H, 8.38; N, 2.73.

The examples given here are for the purpose of illustrating the invention and are not to be considered limiting. Other methods for the synthesis of compounds of the invention will be apparent to those skilled in the art. Thus it is possible to reverse the steps of 17α-propargylation and 11β-arylation by making the 17α-propargyl compound from compound 3, followed by epoxidation and Grignard reaction. This is useful if the aryl substituent is sensitive to lithium/ammonia conditions. Methods known to those skilled in the art are available for other compounds of the invention. For example, the synthesis of 17α-hydroxypropynyl and 17α-trifluoropropynyl analogs may be accomplished from compounds such as 3,3-[1,2-ethanediylbis(oxy)]-17α-ethynyl-20-trimethylsilyloxy-19-norpregna-5(10),9(11)-diene (made as described in U.S. application Ser. No. 09/205,395) by treatment with formaldehyde in the presence of base by standard procedures of acetylene chemistry or by trifluoromethylation as described in the literature for acetylenes. Epoxidation, arylation at C-11, desilylation, mild acid hydrolysis and oxidation of the 20-ol to 20-one leads to the desired trifluoro analog. In the case of the hydroxypropynyl compounds, the primary OH must be protected as for example by acetylation and the protecting group removed at the last step by mild base hydrolysis.

Biology

Biological activity was examined by means of the anti-McGinty test for antiprogestational activity. Immature female rabbits weighing 1000 to 1100 grams were primed with estrogen (5 μg of estradiol in sesame oil as vehicle, given subcutaneously) for 6 days, followed by a surgical procedure to introduce the test compounds into the uterine horn [see for example Teruhiko Tamaya, et al., Local progestational and antiprogestational effects of steroids and their metabolites on the rabbit uterus. *Japanese Journal of Fertility and Sterility* 24:48–51 (1979)]. A single dose of test compound in sesame oil as vehicle, accompanied by a single dose of progesterone (0.3 μg in sesame oil as vehicle) was given. On the third day (dosing being day one) the animals were sacrificed. The uteri were then removed, weighed and a section was kept in 10% formalin for microslide preparation for McPhail Index [M. K. McPhail, The Journal of Physiology, 83: 10 (1934)] determination. Table 1 shows anti-McGinty data (the McPhail Index) for vehicle alone, progesterone alone, and progesterone plus test compounds. Antiprogestational compounds should block the effect of progesterone on the McPhail Index, which is zero in the absence of progesterone. As Table 1 shows, the propynyl compound RTI-6617-041 of this invention is an exceptionally potent antiprogestational agent, having a marked effect at only 0.3 μg dose. It is also markedly more potent than RTI-6617-048, which is its 17α-ethynyl analog, and RTI-6617-040, which is its analog with an acyclic (dimethylamino) group in the 4-position of the 11β-aryl group instead of a cyclic amino group.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A steroid compound of structure I,

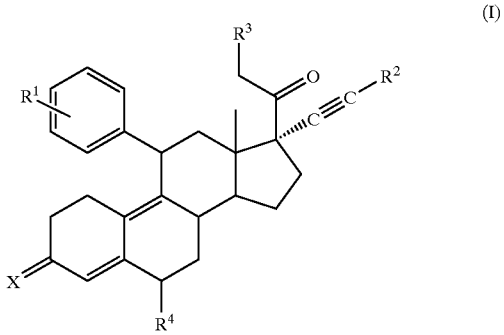

wherein $R^1$ is

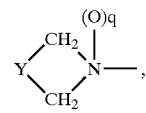

where q is 0 or 1, Y is —(CH$_2$)$_m$— where m is an integer of 0 to 5, or Y is —(CH$_2$)$_n$—Z—(CH$_2$)$_p$— where n is an integer of 0 through 2, p is an integer of 0 through 2 and Z is a heteroatom;

$R^2$ is CH$_3$—, CF$_3$— or HOCH$_2$—;

$B^3$ is H—, CH$_3$—, CH$_3$O—, CH$_3$COO— or halogen;

$R^4$ is H—, CH$_3$—, F— or Cl—; and

X is O, (H,H), NOH or NOCH$_3$, and pharmaceutically acceptable salts thereof.

TABLE 1

Anti-McGinty Assay for Antiprogestational Activity

| Treatment Total Dose | Vehicle[a] n = 3 McPhail Index | Progesterone (P) alone n = 3 McPhail Index | RTI-6617-041[b] + P n = 3 McPhail Index | RTI-6617-048[c] + P n = 3 McPhail Index | RTI-6617-040[d] + P n = 3 McPhail Index |
|---|---|---|---|---|---|
| 0 | 0 +/− 0.0 | | | | |
| 0.3 | | 2.2 +/− 0.3 | 0.78 +/− 0.21 | 1.94 +/− 0.31 | 1.83 +/− 0.36 |
| 3 | | | 0.0 +/− 0.0 | 0.89 +/− 0.3 | 0.0 +/− 0.0 |
| 30 | | | 0.0 +/− 0.0 | 0.0 +/− 0.0 | 0.0 +/− 0.0 |

[a]Sesame oil
[b]11β-[4-(N-Piperidino)phenyl]-17α-(1-propynyl)-19-norpregna-4,9-diene3,20-dione
[c]11β-[4-(N-Piperidino)phenyl]-17α-ethynyl-19-norpregna-4,9-diene-3,20-dione
[d]11β-[4-(N,N-Dimethylamino)phenyl]-17α-(1-propynyl)-19-norpregna-4,9-diene-3,20-dione 2. A steroid compound of structure II

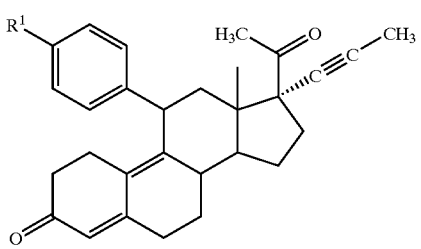

(II)

wherein $R^1$ is selected from the group consisting of N-piperidino, N-pyrrolidino, or N-morpholino.

3. A steroid compound of structure III

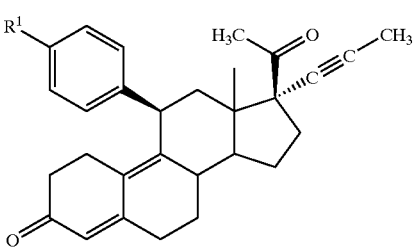

(III)

wherein $R^1$ is selected from the group consisting of N-piperidino, N-pyrrolidino, or N-morpholino.

4. The steroid of claim 1 selected from the group consisting of:

11β-(4-N-morpholinophenyl)-17α-(1-propynyl)-19-norpregna-4,9-diene-3,20-dione;

11β-(4-N-morpholinophenyl)-17α-(3,3,3-trifluoropropyn-1-yl)-19-norpregna-4,9-diene-3,20-dione;

11β-(4-N-morpholinophenyl)-17α-(3-hydroxypropyn-1-yl)-19-norpregna-4,9-diene-3,20-dione;

11β-(4-N-morpholinophenyl)-21-methoxy-17α-(1-propynyl)-19-norpregna-4,9-diene-3,20-dione;

11β-(4-N-morpholinophenyl)-21-methoxy-17α-(3,3,3-trifluoropropyn-1-yl)-19-norpregna-4,9-diene-3,20-dione;

11β-(4-N-morpholinophenyl)-21-methoxy-17α-(3-hydroxypropyn-1-yl)-19-norpregna-4,9-diene-3,20-dione;

11β-(4-N-morpholinophenyl)-21-methoxy-3-oximino-17α-(1-propynyl)-19-norpregna-4,9-dien-20-one;

11β-(4-N-morpholinophenyl)-21-methoxy-3-oximino-17α-(3,3,3-trifluoropropyn-1-yl)-19-norpregna-4,9-dien-20-one;

11β-(4-N-morpholinophenyl)-21-methoxy-3-oximino-17α-(3-hydroxypropyn-1-yl)-19-norpregna-4,9-dien-20-one;

11β-(4-N-morpholinophenyl)-21-methoxy-6-fluoro-17α-(1-propynyl)-19-norpregna-4,9-diene-3,20-dione;

11β-(4-N-morpholinophenyl)-21-methoxy-6-fluoro-17α-(3,3,3-trifluoropropyn-1-yl)-19-norpregna-4,9-diene-3,20-dione;

11β-(4-N-morpholinophenyl)-21-methoxy-6-fluoro-17α-(3-hydroxypropyn-1-yl)-19-norpregna-4,9-diene-3,20-dione;

11β-(4-N-morpholinophenyl)-21-methoxy-6-fluoro-3-oximino-17α-(1-propynyl)-19-norpregna-4,9-dien-20-one;

11β-(4-N-morpholinophenyl)-21-methoxy-6-fluoro-3-oximino-17α-(3,3,3-trifluoropropyn-1-yl)-19-norpregna-4,9-dien-20-one;

11β-(4-N-morpholinophenyl)-21-methoxy-6-fluoro-3-oximino-17α-(3-hydroxypropyn-1-yl)-19-norpregna-4,9-dien-20-one;

11β-(4-N-morpholinophenyl)-21-methoxy-6-methyl-17α-(1-propynyl)-19-norpregna-4,9-diene-3,20-dione;

11β-(4-N-morpholinophenyl)-21-methoxy-6-methyl-17α-(3,3,3-trifluoropropyn-1-yl)-19-norpregna-4,9-diene-3,20-dione;

11β-(4-N-morpholinophenyl)-21-methoxy-6-methyl-17α-(3-hydroxypropyn-1-yl)-19-norpregna-4,9-diene-3,20-dione;

11β-(4-N-morpholinophenyl)-21-methoxy-6-methyl-3-oximino-17α-(1-propynyl)-19-norpregna-4,9-dien-20-one;

11β-(4-N-morpholinophenyl)-21-methoxy-6-methyl-3-oximino-17α-(3,3,3-trifluoropropyn-1-yl)-19-norpregna-4,9-dien-20-one;

11β-(4-N-morpholinophenyl)-21-methoxy-6-methyl-3-oximino-17α-(3-hydroxypropyn-1-yl)-19-norpregna-4,9-dien-20-one;

11β-(4-N-morpholinophenyl)-21-methyl-17α-(1-propynyl)-19-norpregna-4,9-diene-3,20-dione;

11β-(4-N-morpholinophenyl)-21-methyl-17α-(3,3,3-trifluoropropyn-1-yl)-9-norpregna-4,9-diene-3,20-dione;

11β-(4-N-morpholinophenyl)-21-methyl-17α-(3-hydroxypropyn-1-yl)-19-norpregna-4,9-diene-3,20-dione;

11β-(4-N-morpholinophenyl)-21-methyl-3-oximino-17α-(1-propynyl)-19-norpregna-4,9-dien-20-one;

11β-(4-N-morpholinophenyl)-21-methyl-3-oximino-17α-(3,3,3-trifluoropropyn-1-yl)-19-norpregna-4,9-dien-20-one;

11β-(4-N-morpholinophenyl)-21-methyl-3-oximino-17α-(3-hydroxypropyn-1-yl)-19-norpregna-4,9-dien-20-one;

11β-(4-N-morpholinophenyl)-21-methyl-6-fluoro-17α-(1-propynyl)-19-norpregna-4,9-diene-3,20-dione;

11β-(4-N-morpholinophenyl)-21-methyl-6-fluoro-17α-(3,3,3-trifluoropropyn-1-yl)-19-norpregna-4,9-diene-3,20-dione;

11β-(4-N-morpholinophenyl)-21-methyl-6-fluoro-17α-(3-hydroxypropyn-1-yl)-19-norpregna-4,9-diene-3,20-dione;

11β-(4-N-morpholinophenyl)-21-methyl-6-fluoro-3-oximino-17α-(1-propynyl)-19-norpregna-4,9-dien-20-one;

11β-(4-N-morpholinophenyl)-21-methyl-6-fluoro-3-oximino-17α-(3,3,3-trifluoropropyn-1-yl)-19-norpregna-4,9-dien-20-one;

11β-(4-N-morpholinophenyl)-21-methyl-6-fluoro-3-oximino-17α-(3-hydroxypropyn-1-yl)-19-norpregna-4,9-dien-20-one;

11β-(4-N-morpholinophenyl)-6,21-dimethyl-17α-(1-propynyl)-19-norpregna-4,9-diene-3,20-dione;

11β-(4-N-morpholinophenyl)-6,21-dimethyl-17α-(3,3,3-trifluoropropyn1-yl)-19-norpregna-4,9-diene-3,20-dione;

11β-(4-N-morpholinophenyl)-6,21-dimethyl-17α-(3-hydroxypropyn-1-yl)-19-norpregna-4,9-diene-3,20-dione;

11β-(4-N-morpholinophenyl)-6,21-dimethyl-3-oximino-17α-(1-propynyl)-19-norpregna-4,9-dien-20-one;

11β-(4-N-morpholinophenyl)-6,21-dimethyl-3-oximino-17α-(3,3,3-trifluoropropyn-1-yl)-19-norpregna-4,9-dien-20-one;

11β-(4-N-morpholinophenyl)-6,21-dimethyl-3-oximino-17α-(3-hydroxypropyn-1-yl)-19-norpregna-4,9-dien-20-one;

11β-(4-(N-morpholino)phenyl)-3-oximino-17α-(1-propynyl)-19-norpregna-4,9-dien-20-one;

11β-(4-(N-morpholino)phenyl)-3-oximino-17α-(3,3,3-trifluoropropyn-1-yl)-19-norpregna-4,9-dien-20-one;

11β-(4-(N-morpholino)phenyl)-3-oximino-17α-(3-hydroxypropyn-1-yl)-19-norpregna-4,9-dien-20-one;

11β-(4-(N-morpholino)phenyl)-6-fluoro-17α-(1-propynyl)-19-norpregna-4,9-diene-3,20-dione;

11β-(4-(N-morpholino)phenyl)-6-fluoro-17α-(3,3,3-trifluoropropyn-1-yl)-19-norpregna-4,9-diene-3,20-dione;

11β-(4-(N-morpholino)phenyl)-6-fluoro-17α-(3-hydroxypropyn-1-yl)-19-norpregna-4,9-diene-3,20-dione;

11β-(4-(N-morpholino)phenyl)-6-fluoro-3-oximino-17α-(1-propinyl)-19-norpregna-4,9-dien-20-one;

11β-(4-(N-morpholino)phenyl)-6-fluoro-3-oximino-17α-(3,3,3-trifluoropropyn-1-yl)-19-norpregna-4,9-dien-20-one;

11β-(4-(N-morpholino)phenyl)-6-fluoro-3-oximino-17α-(3-hydroxypropyn-1-yl)-19-norpregna-4,9-dien-20-one;

11β-(4-(N-morpholino)phenyl)-6-methyl-17α-(1-propynyl)-19-norpregna-4,9-diene-3,20-dione;

11β-(4-(N-morpholino)phenyl)-6-methyl-17α-(3,3,3-trifluoropropyn-1-yl)-19-norpregna-4,9-diene-3,20-dione;

11β-(4-(N-morpholino)phenyl)-6-methyl-17α-(3-hydroxypropyn-1-yl)-19-norpregna-4,9-diene-3,20-dione;

11β-(4-(N-morpholino)phenyl)-6-methyl-3-oximino-17α-(1-propynyl)-19-norpregna-4,9-dien-20-one;

11β-(4-(N-morpholino)phenyl)-6-methyl-3-oximino-17α-(3,3,3-trifluoropropyn-1-yl)-19-norpregna-4,9-dien-20-one;

11β(4-(N-morpholino)phenyl)-6-methyl-3-oximino-17α-(3-hydroxypropyn-1-yl)-19-norpregna-4,9-dien-20-one;

11β-[4-(N-piperidino)phenyl]-17α-(1-propynyl)-19-norpregna-4,9-diene-3,20-dione;

11β-[4-(N-piperidino)phenyl]17α-(3,3,3-trifluoropropyn-1-yl)-19-norpregna-4,9-diene-3,20-dione;

11β-[4-(N-piperidino)phenyl]-17α-(3-hydroxypropyn-1-yl)-19-norpregna-4,9-diene-3,20-dione;

11β-[4-(N-piperidino)phenyl]-21-methoxy-17α-(1-propynyl)-19-norpregna-4,9-diene-3,20-dione;

11β-[4-(N-piperidino)phenyl]-21-methoxy-17α-(3,3,3-trifluoropropyn-1-yl)-19-norpregna-4,9-diene-3,20-dione;

11β-[4-(N-piperidino)phenyl]-21-methoxy-17α-(3-hydroxypropyn-1-yl)-19-norpregna-4,9-diene-3,20-dione;

11β-[4-(N-piperidino)phenyl]-21-methoxy-3-oximino-17α-(1-propynyl)-19-norpregna-4,9-dien-20-one;

11β-[4-(N-piperidino)phenyl]-21-methoxy-3-oximino-17α-(3,3,3-trifluoropropyn-1-yl)-19-norpregna-4,9-dien-20-one;

11β-[4-(N-piperidino)phenyl]-21-methoxy-3-oximino-17α-(3-hydroxypropyn-1-yl)-19-norpregna-4,9-dien-20-one;

11β-[4-(N-piperidino)phenyl]-21-methoxy-6-fluoro-17α-(1-propynyl)-19-norpregna-4,9-diene-3,20-dione;

11β-[4-(N-piperidino)phenyl]-21-methoxy-6-fluoro-17α-(3,3,3-trifluoropropyn-1-yl)-19-norpregna-4,9-diene-3,20-dione;

11β-[4-(N-piperidino)phenyl]-21-methoxy-6-fluoro-17α-(3-hydroxypropyn-1-yl)-19-norpregna-4,9-diene-3,20-dione;

11β-[4-(N-piperidino)phenyl]-21-methoxy-6-fluoro-3-oximino-17α-(1-propynyl)-19-norpregna-4,9-dien-20-one;

11β-[4-(N-piperidino)phenyl]-21-methoxy-6-fluoro-3-oximino-17α-(3,3,3-trifluoropropyn-1-yl)-19-norpregna-4,9-dien-20-one;

11β-[4-(N-piperidino)phenyl]-21-methoxy-6-fluoro-3-oximino-17α-(3-hydroxypropyn-1-yl)-19-norpregna-4,9-dien-20-one;

11β-[4-(N-piperidino)phenyl]-21-methoxy-6-methyl-17α-(1-propynyl)-19-norpregna-4,9-diene-3,20-dione;

11β-[4-(N-piperidino)phenyl]-21-methoxy-6-methyl-17α-(3,3,3-trifluoropropyn-1-yl)-19-norpregna-4,9-diene-3,20-dione;

11β-[4-(N-piperidino)phenyl]-21-methoxy-6-methyl-17α-(3-hydroxypropyn-1-yl)-19-norpregna-4,9-diene-3,20-dione;

11β-[4-(N-piperidino)phenyl]-21-methoxy-6-methyl-3-oximino-17α-(1-propynyl)-19-norpregna-4,9-dien-20-one;

11β-[4-(N-piperidino)phenyl]-21-methoxy-6-methyl-3-oximino-17α-(3,3,3-trifluoropropyn-1-yl)-19-norpregna-4,9-dien-20-one;

11β-[4-(N-piperidino)phenyl]-21-methoxy-6-methyl-3-oximino-17α-(3-hydroxypropyn-1-yl)-19-norpregna-4,9-dien-20-one;

11β-[4-(N-piperidino)phenyl]-21-methyl-17α-(1-propynyl)-19-norpregna-4,9-diene-3,20-dione;

11β-[4-(N-piperidino)phenyl]-21-methyl-17α-(3,3,3-trifluoropropyn-1-yl)-19-norpregna-4,9-diene-3,20-dione;

11β-[4-(N-piperidino)phenyl]-21-methyl-17α-(3-hydroxypropyn-1-yl)-19-norpregna-4,9-diene-3,20-dione;

11β-[4-(N-piperidino)phenyl]-21-methyl-3-oximino-17α-(1-propynyl)-19-norpregna-4,9-dien-20-one;

11β-[4-(N-piperidino)phenyl]-21-methyl-3-oximino-17α-(3,3,3-trifluoropropyn-1-yl)-19-norpregna-4,9-dien-20-one;

11β-[4-(N-piperidino)phenyl]-21-methyl-3-oximino-17α-(3-hydroxypropyn-1-yl)-19-norpregna-4,9-dien-20-one;

11β-[4-(N-piperidino)phenyl]-21-methyl-6-fluoro-17α-(1-propynyl)-19-norpregna-4,9-diene-3,20-dione;

11β-[4-(N-piperidino)phenyl]-21-methyl-6-fluoro-17α-(3,3,3-trifluoropropyn-1-yl)-19-norpregna-4,9-diene-3,20-dione;

11β-[4-(N-piperidino)phenyl]-21-methyl-6-fluoro-17α-(3-hydroxypropyn-1-yl)-19-norpregna-4,9-diene-3,20-dione;

11β-[4-(N-piperidino)phenyl]-21-methyl-6-fluoro-3-oximino-17α-(1-propynyl)-19-norpregna-4,9-dien-20-one;

11β-[4-(N-piperidino)phenyl]-21-methyl-6-fluoro-3-oximino-17α-(3,3,3-trifluoropropyn-1-yl)-19-norpregna-4,9-dien-20-one;

11β-[4-(N-piperidino)phenyl]-21-methyl-6-fluoro-3-oximino-17α-(3-hydroxypropyn-1-yl)-19-norpregna-4,9-dien-20-one;

11β-[4-(N-piperidino)phenyl]-6,21-dimethyl-17α-(1-propynyl)-19-norpregna-4,9-diene-3,20-dione;

11β-[4-(N-piperidino)phenyl]-21-dimethyl-17α-(3,3,3-trifluoropropyn-1-yl)-19-norpregna-4,9-diene-3,20-dione;

11β-[4-(N-piperidino)phenyl]-6,21-dimethyl-17α-(3-hydroxypropyn-1-yl)-19-norpregna-4,9-diene-3,20-dione;

11β-[4-(N-piperidino)phenyl]-6,21-dimethyl-3-oximino-17α-(1-propynyl)-19-norpregna-4,9-dien-20-one;

11β-[4-(N-piperidino)phenyl]-6,21-dimethyl-3-oximino-17α-(3,3,3-trifluoropropyn-1-yl)-19-norpregna-4,9-dien-20-one;

11β-[4-(N-piperidino)phenyl]-6,21-dimethyl-3-oximino-17α-(3-hydroxypropyn-1-yl)-19-norpregna-4,9-dien-20-one;

11β-[4-(N-piperidino)phenyl]-3-oximino-17α-(1-propynyl)-19-norpregna-4,9-dien-20-one;

11β-[4-(N-piperidino)phenyl]-3-oximino-17α-(3,3,3-trifluoropropyn-1-yl)-19-norpregna-4,9-dien-20-one;

11β-[4-(N-piperidino)phenyl]-3-oximino-17α-(3-hydroxypropyn-1-yl)-19-norpregna-4,9-dien-20-one;

11β-[4-(N-piperidino)phenyl]-6-fluoro-17α-(1-propynyl)-19-norpregna-4,9-diene-3,20-dione;

11β-[4-(N-piperidino)phenyl]-6-fluoro-17α-(3,3,3-trifluoropropyn-1-yl)-19-norpregna-4,9-diene-3,20-dione;

11β-[4-(N-piperidino)phenyl]-6-fluoro-17α-(3-hydroxypropyn-1-yl)-19-norpregna-4,9-diene-3,20-dione;

11β-[4-(N-piperidino)phenyl]-6-fluoro-3-oximino-17α-(1-propynyl)-19-norpregna-4,9-dien-20-one;

11β-[4-(N-piperidino)phenyl]-6-fluoro-3-oximino-17α-(3,3,3-trifluoropropyn-1-yl)-19-norpregna-4,9-dien-20-one;

11β-[4-(N-piperidino)phenyl]-6-fluoro-3-oximino-17α-(3-hydroxypropyn-1-yl)-19-norpregna-4,9-dien-20-one;

11β-[4-(N-piperidino)phenyl]-6-methyl-17α-(1-propynyl)-19-norpregna-4,9-diene-3,20-dione;

11β-[4-(N-piperidino)phenyl]-6-methyl-17α-(3,3,3-trifluoropropyn-1-yl)-19-norpregna-4,9-diene-3,20-dione;

11β-[4-(N-piperidino)phenyl]-6-methyl-17α-(3-hydroxypropyn-1-yl)-19-norpregna-4,9-diene-3,20-dione;

11β-[4-(N-piperidino)phenyl]-6-methyl-3-oximino-17α-(1-propynyl)-19-norpregna-4,9-dien-20-one;

11β-[4-(N-piperidino)phenyl]-6-methyl-3-oximino-17α-(3,3,3-trifluoropropyn-1-yl)-19-norpregna-4,9-dien-20-one;

11β-[4-(N-piperidino)phenyl]-6-methyl-3-oximino-17α-(3-hydroxypropyn-1-yl)-19-norpregna-4,9-dien-20-one;

11β-[4-(N-pyrrolidino)phenyl]-17α-(1-propynyl)-19-norpregna-4,9-diene-3,20-dione;

11β-[4-(N-pyrrolidino)phenyl]-17α-(3,3,3-trifluoropropyn-1-yl)-19-norpregna-4,9-diene-3,20-dione;

11β-[4-(N-pyrrolidino)phenyl]-17α-(3-hydroxypropyn-1-yl)-19-norpregna-4,9-diene-3,20-dione;

11β-[4-(N-pyrrolidino)phenyl]-21-methoxy-17α-(1-propynyl)-19-norpregna-4,9-diene-3,20-dione;

11β-[4-(N-pyrrolidino)phenyl]-21-methoxy-17α-(3,3,3-trifluoropropyn-1-yl)-19-norpregna-4,9-diene-3,20-dione;

11β-[4-(N-pyrrolidino)phenyl]-21-methoxy-17α-(3-hydroxypropyn-1-yl)-19-norpregna-4,9-diene-3,20-dione;

11β-[4-(N-pyrrolidino)phenyl]-21-methoxy-3-oximino-17α-(1-propynyl)-19-norpregna-4,9-dien-20-one;

11β-[4-(N-pyrrolidino)phenyl]-21-methoxy-3-oximino-17α-(3,3,3-trifluoropropyn-1-yl)-19-norpregna-4,9-dien-20-one;

11β-[4-(N-pyrrolidino)phenyl]-21-methoxy-3-oximino-17α-(3-hydroxypropyn-1-yl)-19-norpregna-4,9-dien-20-one;

11β-[4-(N-pyrrolidino)phenyl]-21-methoxy-6-fluoro-17α-(1-propynyl)-19-norpregna-4,9-diene-3,20-dione;

11β-[4-(N-pyrrolidino)phenyl]-21-methoxy-6-fluoro-17α-(3,3,3-trifluoropropyn-1-yl)-19-norpregna-4,9-diene-3,20-dione;

11β-[4-(N-pyrrolidino)phenyl]-21-methoxy-6-fluoro-17α-(3-hydroxypropyn-1-yl)-19-norpregna-4,9-diene-3,20-dione;

11β-[4-(N-pyrrolidino)phenyl]-21-methoxy-6-fluoro-3-oximino-17α-(1-propynyl)-19-norpregna-4,9-dien-20-one;

11β-[4-(N-pyrrolidino)phenyl]-21-methoxy-6-fluoro-3-oximino-17α-(3,3,3-trifluoropropyn-1-yl)-19-norpregna-4,9-dien-20-one;

11β-[4-(N-pyrrolidino)phenyl]-21-methoxy-6-fluoro-3-oximino-17α-(3-hydroxypropyn-1-yl)-19-norpregna-4,9-dien-20-one;

11β-[4-(N-pyrrolidino)phenyl]-21-methoxy-6-methyl-17α-(1-propynyl)-19-norpregna-4,9-diene-3,20-dione;

11β-[4-(N-pyrrolidino)phenyl]-21-methoxy-6-methyl-17α-(3,3,3-trifluoropropyn-1-yl)-19-norpregna-4,9-diene-3,20-dione;

11β-[4-(N-pyrrolidino)phenyl]-21-methoxy-6-methyl-17α-(3-hydroxypropyn-1-yl)-19-norpregna-4,9-diene-3,20-dione;

11β-[4-(N-pyrrolidino)phenyl]-21-methoxy-6-methyl-3-oximino-17α-(1-propynyl)-19-norpregna-4,9-dien-20-one;

11β-[4-(N-pyrrolidino)phenyl]-21-methoxy-6-methyl-3-oximino-17α-(3,3,3-trifluoropropyn-1-yl)-19-norpregna-4,9-dien-20-one;

11β-[4-(N-pyrrolidino)phenyl]-21-methoxy-6-methyl-3-oximino-17α-(3-hydroxypropyn-1-yl)-19-norpregna-4,9-dien-20-one;

11β-[4-(N-pyrrolidino)phenyl]-21-methyl-17α-(1-propynyl)-19-norpregna-4,9-diene-3,20-dione;

11β-[4-(N-pyrrolidino)phenyl]-21-methyl-17α-(3,3,3-trifluoropropyn-1-yl)-19-norpregna-4,9-diene-3,20-dione;

11β-[4-(N-pyrrolidino)phenyl]-21-methyl-17α-(3-hydroxypropyn-1-yl)-19-norpregna-4,9-diene-3,20-dione;

11β-[4-(N-pyrrolidino)phenyl]-21-methyl-3-oximino-17α-(1-propynyl)-19-norpregna-4,9-dien-20-one;

11β-[4-(N-pyrrolidino)phenyl]-21-methyl-3-oximino-17α-(3,3,3-trifluoropropyn-1-yl)-19-norpregna-4,9-dien-20-one;

11β-[4-(N-pyrrolidino)phenyl]-21-methyl-3-oximino-17α-(3-hydroxypropyn-1-yl)-19-norpregna-4,9-dien-20-one;

11β-[4-(N-pyrrolidino)phenyl]-21-methyl-6-fluoro-17α-(1-propynyl)-19-norpregna-4,9-diene-3,20-dione;

11β-[4-(N-pyrrolidino)phenyl]-21-methyl-6-fluoro-17α-(3,3,3-trifluoropropyn-1-yl)-19-norpregna-4,9-diene-3,20-dione;

11β-[4-(N-pyrrolidino)phenyl]-21-methyl-6-fluoro-17α-(3-hydroxypropyn-1-yl)-19-norpregna-4,9-diene-3,20-dione;

11β-[4-(N-pyrrolidino)phenyl]-21-methyl-6-fluoro-3-oximino-17α-(1-propynyl)-19-norpregna-4,9-dien-20-one;

11β-[4-(N-pyrrolidino)phenyl]-21-methyl-6-fluoro-3-oximino-17α-(3,3,3-trifluoropropyn-1-yl)-19-norpregna-4,9-dien-20-one;

11β-[4-(N-pyrrolidino)phenyl]-21-methyl-6-fluoro-3-oximino-17α-(3-hydroxypropyn-1-yl)-19-norpregna-4,9-dien-20-one;

11β-[4-(N-pyrrolidino)phenyl]-6,21-dimethyl-17α-(1-propynyl)-19-norpregna-4,9-diene-3,20-dione;

11β-[4-N-pyrrolidino)phenyl]-6,21-dimethyl-17α-(3,3,3-trifluoropropyn-1-yl)-19-norpregna-4,9-diene-3,20-dione;

11β-[4-(N-pyrrolidino)phenyl]-6,21-dimethyl-17α-(3-hydroxypropyn-1-yl)-19-norpregna-4,9-diene-3,20-dione;

11β-[4-(N-pyrrolidino)phenyl]-6,21-dimethyl-3-oximino-17α-(1-propynyl)-19-norpregna-4,9-dien-20-one;

11β-[4-(N-pyrrolidino)phenyl]-6,21-dimethyl-3-oximino-17α-(3,3,3-trifluoropropyn-1-yl)-19-norpregna-4,9-dien-20-one;

11β-[4-(N-pyrrolidino)phenyl]-6,21-dimethyl-3-oximino-17α-(3-hydroxypropyn-1-yl)-19-norpregna-4,9-dien-20-one;

11β-[4-(N-pyrrolidino)phenyl]-3-oximino-17α-(1-propynyl)-19-norpregna-4,9-dien-20-one;

11β-[4-(N-pyrrolidino)phenyl]-3-oximino-17α-(3,3,3-trifluoropropyn-1-yl)-19-norpregna-4,9-dien-20-one;

11β-[4-(N-pyrrolidino)phenyl]-3-oximino-17α-(3-hydroxypropyn-1-yl)-19-norpregna-4,9-dien-20-one;

11β-[4-(N-pyrrolidino)phenyl]-6-fluoro-17α-(1-propynyl)-19-norpregna-4,9-diene-3,20-dione;

11β-[4-(N-pyrrolidino)phenyl]-6-fluoro-17α-(3,3,3-trifluoropropyn-1-yl)-19-norpregna-4,9-diene-3,20-dione;

11β-[4-(N-pyrrolidino)phenyl]-6-fluoro-17α-(3-hydroxypropyn-1-yl)-19-norpregna-4,9-diene-3,20-dione;

11β-[4-(N-pyrrolidino)phenyl]-6-fluoro-3-oximino-17α-(1-propynyl)-19-norpregna-4,9-dien-20-one;

11β-[4-N-pyrrolidino)phenyl]-6-fluoro-3-oximino-17α-(3,3,3-trifluoropropyn-1-yl)-19-norpregna-4,9-dien-20-one;

11β-[4-(N-pyrrolidino)phenyl]-6-fluoro-3-oximino-17α-(3-hydroxypropyn-1-yl)-19-norpregna-4,9-dien-20-one;

11β-[4-(N-pyrrolidino)phenyl]-6-methyl-17α-(1-propynyl)-19-norpregna-4,9-diene-3,20-dione;

11β-[4-(N-pyrrolidino)phenyl]-6-methyl-17α-(3,3,3-trifluoropropyn-1-yl)-19-norpregna-4,9-diene-3,20-dione;

11β-[4-(N-pyrrolidino)phenyl]-6-methyl-17α-(3-hydroxypropyn-1-yl)-19-norpregna-4,9-diene-3,20-dione;

11β-[4-(N-pyrrolidino)phenyl]-6-methyl-3-oximino-17α-(1-propynyl)-19-norpregna-4,9-dien-20-one;

11β-[4-(N-pyrrolidino)phenyl]-6-methyl-3-oximino-17α-(3,3,3-trifluoropropyn-1-yl)-19-norpregna-4,9-dien-20-one;

11β-[4-(N-pyrrolidino)phenyl]-6-methyl-3-oximino-17α-(3-hydroxypropyn-1-yl)-19-norpregna-4,9-dien-20-one;

21-acetoxy-11β-(4-(N-morpholino)phenyl)-17α-(1-propynyl)-19-norpregna-4,9-diene-3,20-dione;

21-acetoxy-11β-(4-(N-morpholino)phenyl)-17α-(3,3,3-trifluoropropyn-1-yl)-19-norpregna-4,9-diene-3,20-dione;

21-acetoxy-11β-(4-(N-morpholino)phenyl)-17α-(3-hydroxypropyn-1-yl)-19-norpregna-4,9-diene-3,20-dione;

21-acetoxy-11β-(4-(N-morpholino)phenyl)-3-oximino-17α-(1-propynyl)-19-norpregna-norpregna-4,9-dien-20-one;

21-acetoxy-11β-(4-(N-morpholino)phenyl)-3-oximino-17α-(3,3,3-trifluopropyn-1-yl)-19-norpregna-4,9-dien-20-one;

21-acetoxy-11β-(4-(N-morpholino)phenyl)-3-oximino-17α-(3-hydroxypropyn-yl)-19-norpregna-4,9-dien-20-one;

21-acetoxy-11β-(4-(N-morpholino)phenyl)-6-fluoro-17α-(1-propynyl)-19-norpregna-4,9-diene-3,20-dione;

21-acetoxy-11β-(4-(N-morpholino)phenyl)-6-fluoro-17α-(3,3,3-trifluopropyn-1-yl)-19-norpregna-4,9-diene-3,20-dione;

21-acetoxy-11β-(4-(N-morpholino)phenyl)-6-fluoro-17α-(3-hydroxypropyn-1-yl)-19-norpregna-4,9-diene-3,20-dione;

21-acetoxy-11β-(4-(N-morpholino)phenyl)-6-fluoro-3-oximino-17α-(1-propynyl)-19-norpregna-4,9-dien-20-one;

21-acetoxy-11β-(4-(N-morpholino)phenyl)-6-fluoro-3-oximino-17α-(3,3,3-trifluoropropyn-1-yl)-19-norpregna-4,9-dien-20-one;

21-acetoxy-11β-(4-(N-morpholino)phenyl)-6-fluoro-3-oximino-17α-(3-hydroxypropyn-1-yl)-19-norpregna-4,9-dien-20-one;

21-acetoxy-11β-(4-(N-morpholino)phenyl)-6-methyl-17α-(1-propynyl)-19-norpregna-4,9-diene-3,20-dione;

21-acetoxy-11β-(4-(N-morpholino)phenyl)-6-methyl-17α-(3,3,3-trifluoropropyn-1-yl)-19-norpregna-4,9-diene-3,20-dione;

21-acetoxy-11β-(4-(N-morpholino)phenyl)-6-methyl-17α-(3-hydroxypropyn-1-yl)-19-norpregna-4,9-diene-3,20-dione;

21-acetoxy-11β-(4-(N-morpholino)phenyl)-6-methyl-3-oximino-17α-(1-propynyl)-19-norpregna-4,9-dien-20-one;

21-acetoxy-11β-(4-(N-morpholino)phenyl)-6-methyl-3-oximino-17α-(3,3,3-trifluoropropyn-1-yl)-19-norpregna-4,9-dien-20-one;

21-acetoxy-11β-(4-(N-morpholino)phenyl)-6-methyl-3-oximino-17α-(3-hydroxypropyn-1-yl)-19-norpregna-4,9-dien-20-one;

21-acetoxy-11β-[4-(N-piperidino)phenyl]-17α-(1-propynyl)-19-norpregna-4,9-diene-3,20-dione;

21-acetoxy-11β-[4-(N-piperidino)phenyl]-17α-(3,3,3-trifluoropropyn-1-yl)-19-norpregna-4,9-diene-3,20-dione;

21-acetoxy-11β-[4-(N-piperidino)phenyl]-17α-(3-hydroxypropyn-1-yl)-19-norpregna-4,9-diene-3,20-dione;

21-acetoxy-11β-[4-(N-piperidino)phenyl]-3-oximino-17α-(1-propynyl)-19-norpregna-4,9-dien-20-one;

21-acetoxy-11β-[4-(N-piperidino)phenyl]-3-oximino-17α-(3,3,3-trifluoropropyn-1-yl)-19-norpregna-4,9-dien-20-one;

21-acetoxy-11β-[4-(N-piperidino)phenyl]-3-oximino-17α-(3-hydroxypropyn-1-yl)-19-norpregna-4,9-dien-20-one;

21-acetoxy-11β-[4-(N-piperidino)phenyl]-6-fluoro-17α-(1-propynyl)-19-norpregna-4,9-diene-3,20-dione;

21-acetoxy-11β-[4-(N-piperidino)phenyl]-6-fluoro-17α-(3,3,3-trifluoropropyn-1-yl)-19-norpregna-4,9-diene-3,20-dione;

21-acetoxy-11β-[4-(N-piperidino)phenyl]-6-fluoro-17α-(3-hydroxypropyn-1-yl)-19-norpregna-4,9-diene-3,20-dione;

21-acetoxy-11β-[4-(N-piperidino)phenyl]-6-fluoro-3-oximino-17α-(1-propynyl)-19-norpregna-4,9-dien-20-one;

21-acetoxy-11β-[4-(N-piperidino)phenyl]-6-fluoro-3-oximino-17α-(3,3,3-trifluoropropyn-1-yl)-19-norpregna-4,9-dien-20-one;

21-acetoxy-11β-[4-(N-piperidino)phenyl]-6-fluoro-3-oximino-17α-(3-hydroxypropyn-1-yl)-19-norpregna-4,9-dien-20-one;

21-acetoxy-11β-[4-(N-piperidino)phenyl]-6-methyl-17α-(1-propynyl)-19-norpregna-4,9-diene-3,20-dione;

21-acetoxy-11β-[4-(N-piperidino)phenyl]-6-methyl-17β-(3,3,3-trifluoropropyn-1-yl)-19-norpregna-4,9-diene-3,20-dione;

21-acetoxy-11β-[4-(N-piperidino)phenyl]-6-methyl-17α-(3-hydroxypropyn-1-yl)-19-norpregna-4,9-diene-3,20-dione;

21-acetoxy-11β-[4-(N-piperidino)phenyl]-6-methyl-3-oximino-17α-(1-propynyl)-19-norpregna-4,9-dien-20-one;

21-acetoxy-11β-[4-(N-piperidino)phenyl]-6-methyl-3-oximino-17α-(3,3,3-trifluoropropyn-1-yl)-19-norpregna-4,9-dien-20-one;

21-acetoxy-11β-[4-(N-piperidino)phenyl]-6-methyl-3-oximino-17α-(3-hydroxypropyn-1-yl)-19-norpregna-4,9-dien-20-one;

21-acetoxy-11β-[4-(N-pyrrolidino)phenyl]-17α-(1-propynyl)-19-norpregna-4,9-diene-3,20-dione;

21-acetoxy-11β-[4-(N-pyrrolidino)phenyl]-17α-(3,3,3-trifluoropropyn-1-yl)-19-norpregna-4,9-diene-3,20-dione;

21-acetoxy-11β-[4-(N-pyrrolidino)phenyl]-17α-(3-hydroxypropyn-1-yl)-19-norpregna-4,9-diene-3,20-dione;

21-acetoxy-11β-[4-(N-pyrrolidino)phenyl]-3-oximino-17α-(1-propynyl)-19-norpregna-4,9-dien-20-one;

21-acetoxy-11β-[4-(N-pyrrolidino)phenyl]-3-oximino-17α-(3,3,3-trifluoropropyn-1-yl)-19-norpregna-4,9-dien-20-one;

21-acetoxy-11β-[4-(N-pyrrolidino)phenyl]-3-oximino-17α-(3-hydroxypropyn-1-yl)-19-norpregna-4,9-dien-20-one;

21-acetoxy-11β-[4-(N-pyrrolidino)phenyl]-6-fluoro-17α-(1-propynyl)-19-norpregna-4,9-diene-3,20-dione;

21-acetoxy-11β-[4-(N-pyrrolidino)phenyl]-6-fluoro-17α-(3,3,3-trifluoropropyn-1-yl)-19-norpregna-4,9-diene-3,20-dione;

21-acetoxy-11β-[4-N-pyrrolidino)phenyl]-6-fluoro-17α-(3-hydroxypropyn-1-yl)-19-norpregna-4,9-diene-3,20-dione;

21-acetoxy-11β-[4-(N-pyrrolidino)phenyl]-6-fluoro-3-oximino-17α-(1-propynyl)-19-norpregna-4,9-dien-20-one;

21-acetoxy-11β-[4-(N-pyrrolidino)phenyl]-6-fluoro-3-oximino-17α-(3-hydroxypropyn-1-yl)-19-norpregna-4,9-dien-20-one;

21-acetoxy-11β-[4-(N-pyrrolidino)phenyl]-6-fluoro-3-oximino-17α-(3,3,3-trifluoropropyn-1-yl)-19-norpregna-4,9-dien-20-one;

21-acetoxy-11β-[4-(N-pyrrolidino)phenyl]-6-methyl-17α-(1-propynyl)-19-norpregna-4,9-diene-3,20-dione;

21-acetoxy-11β-[4-(N-pyrrolidino)phenyl]-6-methyl-17α-(3,3,3-trifluoropropyn-1-yl)-19-norpregna-4,9-diene-3,20-dione;

21-acetoxy-11β-[4-(N-pyrrolidino)phenyl]-6-methyl-17α-(3-hydroxypropyn-1-yl)-19-norpregna-4,9-diene-3,20-dione;

21-acetoxy-11β-[4-(N-pyrrolidino)phenyl]-6-methyl-3-oximino-17α-(1-propynyl)-19-norpregna-4,9-dien-20-one;

21-acetoxy-11β-[4-(N-pyrrolidino)phenyl]-6-methyl-3-oximino-17α-(3-hydroxypropyn-1-yl)-19-norpregna-4,9-dien-20-one; and 21-acetoxy-11β-[4-(N-pyrrolidino)phenyl]-6-methyl-3-oximino-17α-(3,3,3-trifluoropropyn-1-yl)-19-norpregna-4,9-dien-20-one.

5. A method of treating antiprogestational activity comprising administering a therapeuticaly effective amount of the compound of claim 1, to a patient in need thereof.

6. The method of claim 5, wherein said patient in need thereof has endometriosis or uterine fibroids.

7. The method of claim 5, wherein said patient in need thereof is in need of cervical ripening preparatory to labor and delivery of offspring.

8. The method of claim 5, wherein said patient in need thereof is in need of the control or regulation of fertility.

9. The method of claim 5, wherein said patient in need thereof is in need of hormone replacement therapy.

10. The method of claim 5, further comprising administering one or more pharmacologically active compounds.

11. A method of synthesizing 11β-[4-(N-piperidino)phenyl]-17α-(1-propynyl)-19-norpregna-4,9-diene-3,20-dione by treating 17α-acetoxy-3,3-[1,2-ethanediylbis(oxy)]-5α-hydroxy-11β-[4-(N-piperidino)phenyl]-19-norpregn-9-en-20-one with lithium in liquid ammonia and tetrahydrofuran followed by propargyl bromide to make 3,3-[1,2-ethanediylbis(oxy)]-5α-hydroxy-11β-[4-(N-piperidino)phenyl]-17α-(3-propynyl)-19-norpregn-9-en-20-one and treating this compound with potassium t-butoxide in dimethylsulfoxide to make 3,3-[1,2-ethanediylbis(oxy)]-5α-hydroxy-11β-[4-(N-piperidino)phenyl]-17α-(1-propynyl)-19-norpregn-9-en-20-one and treating this compound with acid.

12. A steroid compound of structure I,
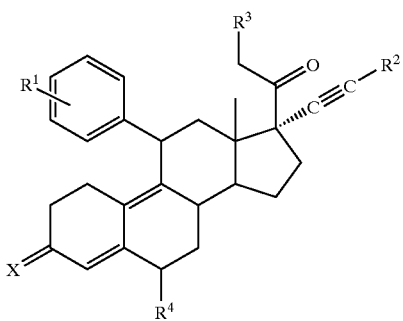
wherein $R^1$ is N-piperidino
$R^2$ is $CH_3$—, $CF_3$— or $HOCH_2$—;
$R^3$ is H—, $CH_3$—, $CH_3O$—, $CH_3COO$— or halogen;
$R^4$ is H—, $CH_3$—, F— or Cl—; and
X is O, (H,H), NOH or $NOCH_3$,
and pharmaceutically acceptable salts thereof.
13. A steroid compound of structure III
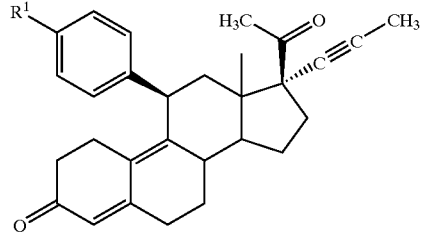
wherein $R^1$ is N-piperidino.
* * * * *